(12) United States Patent
Zhang et al.

(10) Patent No.: US 10,253,103 B2
(45) Date of Patent: Apr. 9, 2019

(54) ANTIBODY SPECIFICALLY BINDING TO GLP-1R AND FUSION PROTEIN THEREOF WITH GLP-1

(71) Applicant: Gmax Biopharm LLC., Hangzhou (CN)

(72) Inventors: Cheng Zhang, Hangzhou (CN); Shuqian Jing, Hangzhou (CN); Hua Zhang, Hangzhou (CN); Xiaofeng Wang, Hangzhou (CN); Chenjiang Yao, Hangzhou (CN)

(73) Assignee: Gmaz Biopharm LLC, Hangzhou (CN)

( * ) Notice: Subject to any disclaimer, the term of this patent is extended or adjusted under 35 U.S.C. 154(b) by 0 days.

(21) Appl. No.: 16/102,552

(22) Filed: Aug. 13, 2018

(65) Prior Publication Data
US 2018/0346585 A1     Dec. 6, 2018

Related U.S. Application Data

(62) Division of application No. 14/911,715, filed as application No. PCT/CN2014/083568 on Aug. 1, 2014, now Pat. No. 10,059,773.

(30) Foreign Application Priority Data

Aug. 13, 2013 (CN) .......................... 2013 1 0350640

(51) Int. Cl.
| | |
|---|---|
| *A61K 38/00* | (2006.01) |
| *A61K 39/00* | (2006.01) |
| *C07K 16/28* | (2006.01) |
| *C07K 14/605* | (2006.01) |

(52) U.S. Cl.
CPC ........ *C07K 16/2869* (2013.01); *C07K 14/605* (2013.01); *A61K 38/00* (2013.01); *A61K 2039/505* (2013.01); *C07K 2317/24* (2013.01); *C07K 2317/34* (2013.01); *C07K 2317/75* (2013.01); *C07K 2319/00* (2013.01); *C07K 2319/31* (2013.01)

(58) Field of Classification Search
CPC .............. C07K 16/2869; C07K 14/605; C07K 2319/31; C07K 2317/24; C07K 2317/34; C07K 2319/00; C07K 2317/75; A61K 2039/505; A61K 38/00
See application file for complete search history.

(56) References Cited

U.S. PATENT DOCUMENTS

| | | | |
|---|---|---|---|
| 5,899,883 A | 5/1999 | Chern et al. | |
| 6,006,753 A | 12/1999 | Efendic | |
| 6,191,102 B1 | 2/2001 | Dimarchi et al. | |
| 6,277,819 B1 | 8/2001 | Efendic | |
| 6,348,447 B1 | 2/2002 | Hellstrom et al. | |
| 6,989,148 B2 | 1/2006 | Dupre | |
| 7,993,642 B2 | 8/2011 | Tsunoda et al. | |
| 2003/0224983 A1 | 12/2003 | Nielsen | |
| 2006/0275288 A1 | 12/2006 | Grihalde et al. | |
| 2009/0098130 A1 | 4/2009 | Bradshaw et al. | |
| 2009/0214534 A1 | 8/2009 | Holmes et al. | |
| 2011/0020345 A1 | 1/2011 | Herring et al. | |
| 2011/0098443 A1 | 4/2011 | Karyn et al. | |
| 2012/0270782 A1 | 10/2012 | Gopinath et al. | |

FOREIGN PATENT DOCUMENTS

| | | |
|---|---|---|
| WO | 2000/016797 A2 | 3/2000 |
| WO | 2002/046227 A2 | 6/2002 |
| WO | 2006/059106 A2 | 6/2006 |
| WO | 2006/068910 A1 | 6/2006 |
| WO | 2007/039140 A1 | 4/2007 |

OTHER PUBLICATIONS

Bonner-Weir, "Life and death of the pancreatic beta cells," Trends Endocrinol Metab., 2000, 11, 375-378.
Brown et al., "Tolerance of single, but not multiple, amino acid replacements in antibody VH CDR 2: a means of minimizing B cell wastage from somatic hypermutation?" J. Immunol. 1996, 156, 3285-3291.
Defronzo, "Lilly lecture 1987. The triumvirate: beta-cell, muscle, liver. A collusion responsible for NIDDM," Diabetes, 1988, 37, 667-687.
Doyle et al., "Mechanisms of action of glucagon-like peptide 1 in the pancreas," Pharmacol. Ther., 2007, 113, 546-593.
Drucker et al., "Glucagon-like peptide I stimulates insulin gene expression and increases cyclic AMP levels in a rat islet cell line," Proc. Natl. Acad. Sci. USA, 1987, 84, 3434-3438.
Hui et al., "Glucagon-like peptide-1 inhibits apoptosis of insulin-secreting cells via a cyclic 5'-adenosine monophosphate-dependent protein kinase A- and a phosphatidylinositol 3-kinase-dependent pathway," Endocrinology, 2003, 144, 1444-1455.
Kahn and Goldfine, "Molecular determinants of insulin action," J. Diabetes Complications, 1993, 7, 92-105.
Kahn et al., "Obesity, body fat distribution, insulin sensitivity and Islet beta-cell function as explanations for metabolic diversity," J. Nutr., 2001, 131, 354S-360S.
Lam et al., "Free fatty acid-induced hepatic insulin resistance: a potent role for protein kinase C-delta," Am. J. Physiol. Endocrinol. Metab., 2002, 283, E682-E691.
Lin et al., "Molecular modeling of the three-dimensional structure of GLP-1R and its interactions with several agonists," J. Mol. Model., 2009, 15, 53-65.
Lund et al., "Glucagon-like peptide-1 receptor agonists for the treatment of type 2 diabetes: differences and similarities," Eur. J. Intern. Med., 2014, 25, 407-414.

(Continued)

*Primary Examiner* — Ruixiang Li
(74) *Attorney, Agent, or Firm* — Jones Day

(57) ABSTRACT

Disclosed in the present invention is an antibody specifically binding to GLP-1R and a fusion protein thereof with GLP-1. The fusion proteins can effectively bind to a human GLP-1R receptor and activate a receptor signaling pathway, thus are useful for treating diabetes, excessive weight, obesity and related disorders thereof.

31 Claims, 3 Drawing Sheets
Specification includes a Sequence Listing.

(56) References Cited

OTHER PUBLICATIONS

Nauck et al., "Glucagon-like peptide 1 (GLP-1) as a new therapeutic approach for type 2-diabetes," Exp. Clin. Endocrinol. Diabetes., 1997, 105, 187-195.

Orskov et al., "Tissue and plasma concentrations of amidated and glycine-extended glucagon-like peptide I in humans," Diabetes, 1994, 43, 535-539.

Paul, Fundamental Immunology, 3rd Edition, 1993, pp. 292-295.

Perfetti et al., "Glucagon-like peptide-1 induces cell proliferation and pancreatic-duodenum homeobox-1 expression and increases endocrine cell mass in the pancreas of old, glucose-intolerant rats," Endocrinology (2000) 141:4600-4605.

Rudikoff et al., "Single amino acid substitution altering antigen-binding specificity," Proc. Natl. Acad. Sci. U.S.A. 1982, 79, 1979-1983.

Samson et al., "GLP-1R agonist therapy for diabetes: benefits and potential risks," Curr. Opin. Endocrinol. Diabetes Obes., 2013, 20, 87-97.

Todd et al., "Glucagon-like peptide-1 (GLP-1): a trial of treatment in non-insulin-dependent diabetes mellitus," Eur. J. Clin. Invest., 1997, 27, 533-536.

Unger et al., "Role of glucagon in diabetes," Arch. Intern. Med., 1977, 137, 482-491.

Vajdos et al., "Comprehensive functional maps of the antigen-binding site of an anti-ErbB2 antibody obtained with shotgun scanning mutagenesis," J. Mol. Biol. 2002, 320, 415-428.

Verspohl, "Novel pharmacological approaches to the treatment of type 2 diabetes," Pharmacol. Rev., 2012, 64, 188-237.

Wettergren et al., "Truncated GLP-1 (proglucagon 78-107-amide) inhibits gastric and pancreatic functions in man," Dig. Dis. Sci., 1993, 38, 665-673.

Weyer et al., "The natural history of insulin secretory dysfunction and insulin resistance in the pathogenesis of type 2 diabetes mellitus," J. Clin. Invest., 1999, 104, 787-794.

ANTIBODY SPECIFICALLY BINDING TO GLP-1R AND FUSION PROTEIN THEREOF WITH GLP-1

CROSS REFERENCE TO RELATED APPLICATIONS

This application is a divisional application of U.S. application Ser. No. 14/911,715, which is a National Stage of International Application No. PCT/CN2014/083568, filed Aug. 1, 2014, which claims the benefit of the priority of Chinese Patent Application No. 201310350640.0, filed Aug. 13, 2013; the disclosure of each of which is incorporated herein by reference in its entirety.

REFERENCE TO A SEQUENCE LISTING

The present specification is being filed with a Sequence Listing in Computer Readable Form (CRF), which is entitled 14254-011-999_SEQLIST.txt of 70,497 bytes in size and was created Aug. 10, 2018; the content of which is incorporated herein by reference in its entirety.

FIELD

The present invention relates to the technical field of antibodies, especially relating to an antibody specifically binding to GLP-1R and fusion proteins thereof with GLP-1.

BACKGROUND

Typical symptoms of type II diabetes include the following three aspects: 1) the peripheral insulin resistance, mainly the responsiveness of bone and muscle to insulin is reduced, leading to affected glucose output of these tissues (Kahn and Goldfine, J Diabetes Complication (1993) 7:92-105; Weyer et al., J Clin Invest. (1999) 104:787-794); 2) excessive hepatic glucose production, the regulation of liver cells to the responsiveness of insulin is reduced (Kahn and Goldfine, J Diabetes Complication (1993) 7:92-105; Lam et al., Am J Physiol Endocrinol Metab. (2009) 11:375-378) and the excessive secretion of glucagon (Unger and Orci, Arch Intern Med. (1977) 137:482-491); and 3) disorders of pancreatic islet beta cells, at an earlier stage of a disease, an increase in beta cell proliferation and insulin secretion compensates the impact of insulin resistance on blood sugar (Bonner-Weir, Trends Endocrinol Metab. (2000) 11:375-378), but with the increase of time and the degree of insulin resistance, depletion of beta cells occurs, followed by decreased insulin secretion, thus leading to type II diabetes (DeFronzo, Diabetes. (1988) 37:667-687; Kahn et al., J Nutr. (2001) 131:354S-360S).

Glucagon like peptide-1 (GLP-1) is a peptide containing 30 amino acids. It is secreted from L intestinal cells in response to the intake of glucose (Orskov et al., Diabetes (1994) 43:535-539; Drucker et al., Proc. Natl. Acad. Sci. USA (1987) 84:3431-3438). After the secretion upon stimulation, GLP-1 binds to pancreatic GLP-1R (glucagon like peptide-1 receptor) to activate the downstream adenylate cyclase signaling pathway to promote the synthesis and secretion of insulin. GLP-1 secretion also reduces gastric emptying, thereby reducing the amount of glucose into the circulatory system after food digestion (Wettergren et al., Dig. Dis. Sci. (1993) 38:665-673). In mice and in patients with type I and type II diabetes, GLP-1 increases insulin secretion and reduces blood sugar concentration (Nauck et al., Diabetes. (1997) 105:187-195; Todd et al., Eur J Clin Invest. (1997) 27:533-536). Studies have shown that GLP-1 can also inhibit apoptosis of pancreatic beta cells and promote their proliferation (Perfetti et al., Endocrinology (2000) 141:4600-4605; Hui et al., Endocrinology (2003) 144:1444-1455). The feasibility and efficacy of GLP-1 for the treatment of diabetes patients have been proved clinically (Samson and Garber, Curr Opin Endocrinol Diabetes Obes. (2013) 20:87-97). There are also patents (U.S. Pat. No. 5,899,883 and U.S. Pat. No. 6,989,148) disclosing methods for the treatment of diabetes by using GLP-1 and its derivatives. However, GLP-1 has a short half-life in vivo and does not have good therapeutic effects.

SUMMARY

One objective of the present invention is to provide an antibody specifically binding to GLP-1R.

The second objective of the present invention is to provide a fusion protein of an antibody specifically binding to GLP-1R with GLP-1, which can extend the half-life of GLP-1 in vivo to retain the biological activity of GLP-1. At the same time, the fusion protein formed by GLP-1 and the antibody specifically binding to GLP-1R has the molecular targeting properties provided by the antibody. Furthermore, the immunogenicity of the antibody is also lower than that of other fusion partners.

To solve the technical problems mentioned above, the present invention provides the following technical solutions.

An antibody specifically binding to GLP-1R comprises an amino acid sequence selected from:

(a) a light chain CDR3 sequence selected from:
light chain CDR3 sequences differing by no more than three amino acid additions, substitutions and/or deletions in total from one of L1-L13 light chain CDR3 sequences: SEQ ID NO: 46 to SEQ ID NO: 53; preferably, light chain CDR3 sequences differing by no more than two amino acid additions, substitutions and/or deletions in total from one of L1-L13 light chain CDR3 sequences: SEQ ID NO: 46 to SEQ ID NO: 53; and more preferably, light chain CDR3 sequences differing by one amino acid addition, substitution and/or deletion from one of L1-L13 light chain CDR3 sequences: SEQ ID NO: 46 to SEQ ID NO: 53;

(b) a heavy chain CDR3 sequence selected from:
heavy chain CDR3 sequences differing by no more than four amino acid additions, substitutions and/or deletions in total from one of H1-H13 heavy chain CDR3 sequences: SEQ ID NO: 20 to SEQ ID NO: 27; preferably, heavy chain CDR3 sequences differing by no more than three amino acid additions, substitutions and/or deletions in total from one of H1-H13 heavy chain CDR3 sequences: SEQ ID NO: 20 to SEQ ID NO: 27; more preferably, heavy chain CDR3 sequences differing by no more than two amino acid additions, substitutions and/or deletions in total from one of H1-H13 heavy chain CDR3 sequences: SEQ ID NO: 20 to SEQ ID NO: 27; and further preferably, heavy chain CDR3 sequences differing by one amino acid addition, substitution and/or deletion in total from one of H1-H13 heavy chain CDR3 sequences SEQ ID NO: 20 to SEQ ID NO: 27; and (c) a light chain CDR3 sequence from (a) and a heavy chain CDR3 sequence from (b).

Preferably, the antibody further comprises one or more amino acid sequences selected from:

(a) a light chain CDR1 sequence selected from:
light chain CDR1 sequences differing by no more than three amino acid additions, substitutions and/or deletions from one of L1-L13 light chain CDR1 sequences: SEQ ID NO: 28 to SEQ ID NO: 37; preferably, light chain CDR1 sequences differing by no more than two amino acid additions, substitutions and/or deletions in total from one of L1-L13 light chain CDR1 sequences: SEQ ID NO: 28 to SEQ ID NO: 37; and more preferably, light chain CDR1 sequences differing by one amino acid addition, substitution and/or deletion from one of L1-L13 light chain CDR1 sequences: SEQ ID NO: 28 to SEQ ID NO: 37;

(b) a light chain CDR2 sequence selected from:
light chain CDR2 sequences differing by no more than two amino acid additions, substitutions and/or deletions from one of L1-L13 light chain CDR2 sequences: SEQ ID NO: 38 to SEQ ID NO: 45; and preferably, light chain CDR2 sequences differing by one amino acid addition, substitution and/or deletion from one of L1-L13 light chain CDR2 sequences SEQ ID NO: 38 to SEQ ID NO: 45;

(c) a heavy chain CDR1 sequence selected from:
heavy chain CDR1 sequences differing by no more than two amino acid additions, substitutions and/or deletions from one of H1-H13 heavy chain CDR1 sequences: SEQ ID NO: 6 to SEQ ID NO: 12; and preferably, heavy chain CDR1 sequences differing by one amino acid addition, substitution and/or deletion from one of H1-H13 heavy chain CDR1 sequences: SEQ ID NO: 6 to SEQ ID NO: 12; and (d) a heavy chain CDR2 selected from:
heavy chain CDR2 sequences differing by no more than three amino acid additions, substitutions and/or deletions from one of H1-H13 heavy chain sequences: SEQ ID NO: 13 to SEQ ID NO: 19; preferably, heavy chain CDR2 sequences differing by no more than two amino acid additions, substitutions and/or deletions in total from one of H1-H13 heavy chain CDR2 sequences: SEQ ID NO: 13 to SEQ ID NO: 19; and more preferably, heavy chain CDR2 sequences differing by one amino acid addition, substitution and/or deletion from one of H1-H13 heavy chain CDR2 sequences: SEQ ID NO: 13 to SEQ ID NO: 19.

An antibody specifically binding to GLP-1R comprises an amino acid sequence selected from:
(a) one or more light chain variable regions selected from:
  i. light chain CDR1 sequences: SEQ ID NO: 28 to SEQ ID NO: 37;
  ii. light chain CDR2 sequences: SEQ ID NO: 38 to SEQ ID NO: 45; and
  iii. light chain CDR3 sequences: SEQ ID NO: 46 to SEQ ID NO: 53;
(b) one or more heavy chain variable regions selected from:
  i. heavy chain CDR1 sequences: SEQ ID NO: 6 to SEQ ID NO: 12;
  ii. heavy chain CDR2 sequences: SEQ ID NO: 13 to SEQ ID NO: 19; and
  iii. heavy chain CDR3 sequences: SEQ ID NO: 20 to SEQ ID NO: 27; and
(c) a light chain variable domain sequence from (a) and a heavy chain variable domain sequence from (b).

An antibody specifically binding to GLP-1R comprises an amino acid sequence selected from:
(a) a light chain variable region selected from:
  i. amino acid sequences that are at least 80% identical to any of L1-L13 light chain variable region sequences: SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105; and
  ii. amino acid sequences encoded by polynucleotide sequences that are at least 80% identical to any of the polynucleotide sequences encoding for L1-L13 light chain variable region sequences: SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104;

(b) a heavy chain variable domain sequence selected from:
  i. amino acid sequences that are at least 80% identical to any of H1-H13 heavy chain variable region sequences: SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79; and
  ii. an amino acid sequences encoded by polynucleotide sequences that are at least 80% identical to any of the polynucleotide sequences encoding for H1-H13 heavy chain variable region sequences: SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78; and (c) a light chain variable region sequence from (a) and a heavy chain variable region sequence from (b).

Preferably, the antibody further comprises an amino acid sequence selected from:
(a) L1-L13 light chain variable region sequences: SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105;
(b) H1-H13 heavy chain variable region sequences: SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79; and
(c) a light chain variable region sequence from (a) and a heavy chain variable region sequence from (b).

Preferably, the combination (c) of a light chain variable region sequence (a) and a heavy chain variable region sequence (b) is selected from L1H1, L2H2, L3H3, L4H4, L5H5, L6H6, L7H7, L8H8, L9H9, L10H10, L11H11, L12H12, L13H13.

Preferably, the antibody also comprises an amino acid sequence selected from:
(a) light chain constant region amino acid sequence: SEQ ID NO 106;
(b) light chain constant region amino acid sequence: SEQ ID NO 107;
(c) heavy chain constant region amino acid sequence: SEQ ID NO 108;
(d) heavy chain constant region amino acid sequence: SEQ ID NO 109;
(e) light chain constant region amino acid sequence: SEQ ID NO 106 and heavy chain constant region amino acid sequence: SEQ ID NO 108;
(f) light chain constant region amino acid sequence: SEQ ID NO 107 and heavy chain constant region amino acid sequence of SEQ ID NO 108;
(g) light chain constant region amino acid sequence: SEQ ID NO 106 and heavy chain constant region amino acid sequence: SEQ ID NO 109; and
(h) light chain constant region amino acid sequence: SEQ ID NO 107 and heavy chain constant region amino acid sequence: SEQ ID NO 109.

Preferably, the antibody is selected from murine antibodies, human antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, tetra-chain antibodies, Fab fragments, F(fa')x fragments, domain antibodies, IgD antibodies, IgE antibodies, IgM antibodies, IgG1 antibodies, IgG2 antibodies, IgG3 antibodies, and IgG4 antibodies.

A GLP-1 fusion protein comprising GLP-1 and an antibody of the present invention, wherein GLP-1 comprises an amino acid sequence selected from SEQ ID NO:1, SEQ ID NO: 2, SEQ ID NO: 3, SEQ ID NO: 4, SEQ ID NO: 5, SEQ ID NO:127.

Preferably, GLP-1 is fused with the light chain and/or heavy chain of the antibody of the present invention via N'—R1-L-R2-C', N'—R2-L-R1-C' or N'—R2-R1$_r$-C';

wherein L is a peptide linker sequence, comprising a full-length, partial or repeated amino acid sequence selected from LK1-LK3 amino acid sequences: SEQ ID NO: 110, SEQ ID NO: 111, SEQ ID NO: 112;

R1 is an amino acid sequence of GLP-1;

R1$_r$ is a reverse amino acid sequence of GLP-1;

R2 is an amino acid sequence of the light chain or heavy chain of the antibody of the present invention;

C' represents the hydroxyl terminal of the GLP-1 fusion protein polypeptide chain;

N' represents the amino terminal of the GLP-1 fusion protein polypeptide chain.

A polynucleotide encodes a GLP-1 fusion protein of the present invention.

A vector comprises a polynucleotide of the present invention.

A host cell comprises a vector of the present invention.

A pharmaceutical composition comprises a GLP-1 fusion protein of the present invention and a pharmaceutically acceptable carrier.

Use of a pharmaceutical composition comprising or based on an antibody or GLP-1 fusion protein of the present invention in the preparation of a medicament for preventing or treating non-insulin-dependent diabetes is disclosed.

Given that the key role of GLP-1R plays in the use of glucagon like peptide-1 for the regulation and control of blood glucose levels in type II diabetes patients, and that its significant therapeutic characteristic is the ability of stimulating insulin secretion without the associated risk of hypoglycaemia. GLP-1 is fused with an antibody specifically binding to GLP-1R in the present invention, thereby prolonging the half-life of GLP-1 in vivo to retain the biological activity of GLP-1. At the same time, the fusion protein formed by GLP-1 and the antibody specifically binding to GLP-1R has the molecular targeting properties provided by the antibody. Furthermore, the immunogenicity of the antibody is also lower than that of other fusion partners.

The beneficial effects of the present invention are as follows: GLP-1 is capable of fusing with an antibody specifically binding to GLP-1R, thus prolonging the half-life of GLP-1 in vivo to retain the biological activity of GLP-1. At the same time, the fusion protein formed by GLP-1 and the antibody specifically binding to GLP-1R has the molecular targeting properties provided by the antibody. Furthermore, the immunogenicity of the antibody is also lower than that of other fusion partners.

DETAILED DESCRIPTION

The present invention is directed to the disadvantage that GLP-1 is quickly removed by dipeptidyl peptidase (DPP-IV) in vivo and has insufficient efficacy, and applies antibodies of GLP-1R to fuse with GLP-1 so as to enhance the half-life and biological activity of GLP-1. Antibodies used for the fusion do not hinder the binding of GLP-1 with receptors, can specifically facilitate the biological activity of GLP-1R, and due to their high affinity to receptors and stability, are capable of enhancing the long lasting local concentrations of GLP-1 around the receptors and thereby significantly increasing its effective time and potency for binding to the receptor. At the same time, the fusion with the antibody increases the steric hindrance for DPP-IV to recognize or capture GLP-1, thus reducing the elimination rate of GLP-1 in vivo and increasing the effective time of GLP-1. According to literature reports (Lin and Wang, J of Molecular Modeling (2009) 15:53-65), the release of the articulation state between the N-terminal extracellular region of GLP-1R and the transmembrane region thereof is an essential step for GLP-1 to enter the binding site to GLP-1R and become biologically active. As described in the present invention, the binding of the antibody to GLP-1R is largely involved in the N-terminal extracellular region of the receptor, and the binding thereof to the receptor helps the release of said articulation state and can facilitate the access of GLP-1. Accordingly, the fusion of GLP-1 with the antibody targeting GLP-1R increases the half-life and affinity potency of GLP-1 to result a stronger biological activity, and thus is an important innovation superior to the GLP-1 therapy. More importantly, some of the antibodies themselves used in the present invention have the biological characteristics of enhancing GLP-1 activation of GLP-1R in the presence of GLP-1. Because of some of the reasons above, the GLP-1 fusion protein in the present invention may be a more effective activator of GLP-1R than GLP-1.

It is a common concern that the repetitive administration of a fusion protein for a long time may elicit antigenicity. This is especially a concern in the case of GLP-1 fusion protein therapy, because once a patient is diagnosed with diabetes, the patient is to receive a life-long treatment for the disease. In addition, if the Fc parts of the immune globulin retain undesirable effector function, the Fc fusion protein therapy can be a concern. Via computer-assisted 3D structure prediction of an immune globulin, and antibody sequence optimization and humanization, the identified specific GLP-1 fusion proteins no longer have effector function and thus have reduced risk of inducing immune response after repeated and long-term administration. As discussed in the present invention, the amino acid of GLP-1 moiety is preferably fused with light and heavy chains of the antibodies through glycine and serine rich peptide linker. Because of having smaller side chains, glycine and serine enable the peptide linker sequence considerably flexible, reducing the rigidity between GLP-1 and the corresponding positions of the antibody, thus GLP-1 can interact with GLP-1R freely. At the same time, the presence of the peptide linker separates GLP-1 from the antibody, thus avoiding the interaction of the two domains. The glycine and serine appear alternately to avoid excessive repetition, in order not to introduce undesirable immunogenicity to the fusion protein, however, the peptide linker inevitably increases the immunogenicity of the fusion protein in vivo, and it is of great importance to select the length of the peptide linker so as to balance structure flexibility and immunogenicity. Accordingly, the present invention provides three different lengths of peptide linkers for fusion. At the same time, the present invention provides different ways of linking GLP-1 with the antibody by using peptide linkers for fusion, and the patterns of the formed GLP-1 fusion proteins would include:

1) a fusion protein with GLP-1 and a light chain linked in the form of N'—R1-L-R2-C';

2) a fusion protein with GLP-1 and a light chain linked in the form of N'—R2-L-R1-C';

3) a fusion protein with GLP-1 and a light chain linked in the form of N'—R2-L-R1r-C';

4) a fusion protein with GLP-1 and a heavy chain linked in the form of N'—R1-L-R2-C';

5) a fusion protein with 1) and 4) at the same time;

6) a fusion protein with 2) and 4) at the same time;

7) a fusion protein with 3) and 4) at the same time.

Within the scope of the present invention, the DNA encoding the GLP-1 is linked to full length/variable region/ fragment light chain or full length/variable region/full length heavy chain DNA of said antibody, via the DNA encoding the peptide linker sequence, forming a fused light chain or fused heavy chain DNA, furthermore, at the 5' end of the light chain DNA, the DNA encoding the signal peptide is also introduced to form a gene based on which the mutant/ wild type GLP-1 can be linked to antibody sequences. In the present invention, the GLP-1 sequences obtained by the method of gene synthesis are linked to the peptide linker as well as antibody light or heavy chain DNA through the method of PCR. The light or heavy chain variable region sequences of the antibodies to GLP-1R are obtained from specific hybridoma cells through the method of PCR followed by being linked to the constant region DNA of specific antibody subtype. The constant region DNA of the wild type antibody subtype can be obtained from a specific clone library and used as the basis of sequence optimization. After cloned into an expression vector, genes used for expressing the fusion protein described herein are used for producing and expressing the fusion proteins. After the light chain and heavy chain expression vectors are paired during expression, the DNA carrying the genes are co-transfected or transformed into a host cell. The promoter is induced by optimal adaption. The transformants or genes for amplifying desired sequences are cultured in a proper medium at an appropriate pH and temperature. DNA is usually introduced by commonly used methods, such as $CaPO_4$, electroporation, and PEI etc.

The suitable host cells, suitable for the expression of the nucleic acid within the vector described herein, include higher eukaryotic cells, and the examples of mammalian host cell line for expression include Chinese hamster ovary cell line (CHO) and human embryonic kidney cell (HEK293, or HEK293 cell line cultured in a suspension), and the signal peptide at the N-terminal of the light chain guides the secretion of recombinant fusion proteins from the mammalian host cell line. The vector for expression or cloning carries the selection marker that enables its continuously replication in host cells and is used to screen cells capable of integrating the fusion protein encoding nucleic acid, and promoter that effectively links with the fusion protein encoding sequence and guides mRNA synthesis. One example is to use a vector carrying antibiotics resistance and Hepatitis B virus and simian virus promoter (SV40) to select CHO host cells stably expressing the fusion proteins.

After host cell lines have expressed fusion proteins, the present invention adopts an affinity chromatographic method to purify the part secreted thereby in the cell culture supernatant. In an example of the invention, the fusion protein fused with full-length antibody is captured by a protein G affinity chromatography column and then eluted from the chromatography column by low pH followed by collection. Mild elution conditions help to prevent denaturing of the protein.

The fusion protein of the present invention can be formulated with one or more excipients. The fusion protein of the present invention can be combined with a pharmaceutically acceptable buffer having adjusted pH that provides acceptable stability and is suitable for administration (such as parenteral administration). Optionally, one or more pharmaceutically acceptable antimicrobial reagents may be added. Preferred pharmaceutically acceptable antimicrobial reagents are m-cresol and phenol. One or more pharmaceutically acceptable salt solution can be added to adjust the ionic strength or tension. One or more excipients may be added to further adjust the isotonicity of the formulation. Glycerin is an example of excipients for adjusting the isotonicity. “Pharmaceutically acceptable” means being suitable for administration to human or other animals, and therefore free of toxic ingredients or undesirable pollutants and not interfere with the activity of the active compounds therein.

The fusion protein of the invention can be prepared in a solution preparation or in a lyophilized powder that can be reconstituted with appropriate diluent. Lyophilized dosage form is one of the formulation types in which the fusion protein is stable, with or without the buffering capacity to maintain the pH over its intended in-use shelf-life of the reconstituted product. The solution comprising fusion proteins discussed herein is preferably isotonic before lyophilization to enable the formation of an isotonic solution after reconstitution.

A pharmaceutically acceptable salt form of the fusion proteins of the present invention is within the scope of the present invention. Commonly employed acids to form acid addition salts are inorganic acids, such as hydrochloric acid, hydrobromic acid, hydroiodic acid, sulfuric acid, and phosphoric acid; and organic acids such as p-toluenesulfonic acid, methanesulfonic acid, oxalic acid, p-bromophenylsulfonic acid, carbonic acid, succinic acid, citric acid, benzoic acid, and acetic acid. Preferable acid addition salts are those formed with inorganic acids, such as hydrochloric acid and hydrobromic acid.

Base addition salts include those derived from inorganic bases, such as ammonium, base or alkali earth metal hydroxide, carbonate, and bicarbonate. Such bases useful in preparing the salt solution of the present invention thus include sodium hydroxide, potassium hydroxide, ammonium hydroxide, potassium carbonate, and the like.

The fusion proteins of the present invention have biological activity. Biological activity refers to the ability of the fusion proteins to bind and activate the GLP-1R in vivo and stimulate stress response. Responses include but not limited to, increased secretion of insulin, suppression of secretion of glucagon, inhibition of appetite, weight loss, induction of satiety, inhibition of apoptosis, and induction of pancreatic beta cell proliferation and pancreatic beta cell differentiation. A number of representative GLP-1 fusion proteins are tested for in vitro and in vivo activities. First, step 4 (FIG. 1) provides data on a fluorescence detection assay of the fusion protein to interact with the GLP-1R. Then, step 12 provides in vitro activity test of the fusion protein interacting with and activating human GLP-1R. In this set of experiments, CHO cells over-expressing human GLP-1R were used. Activation of the GLP-1R in these cells causes adenylyl cyclase activation which in turn induces expression of a reporter gene driven by a cAMP response element (CRE). Step 12 (FIG. 2) provides the data where the reporter gene is luciferase. In vitro experimental data indicate that the fusion proteins are capable of binding and activating GLP-1R and appear to be more effective than the native GLP-1 in vitro. Step 13 (FIG. 3) provides the data of blood glucose concentration change of the mice 16 hours (hr) after being intraperitoneally administrated with one of the fusion proteins of the present invention. The in vivo data generated on mice of step 13 demonstrate the activity of the fusion protein and its longer half-life than the native GLP-1.

Administration of the fusion protein may be via any route known to be effective by the physician of ordinary skill. Peripheral parenteral administration is one of such methods. Parenteral administration is commonly understood in medical literature as the injection of a dosage form into the body with a sterile syringe or other mechanical device such as an infusion pump. Peripheral parenteral routes include intravenous, intramuscular, subcutaneous, and intraperitoneal routes of administration.

The fusion proteins of the present invention can also be administrated by oral, rectal, nasal, or lower respiratory routes, which are non-parenteral routes. Of these non-parenteral routes, the lower respiratory route and the oral route are preferred.

The fusion proteins of the present invention can be used to treat a wide variety of diseases and conditions. The fusion proteins of the present invention primarily exert their biological effects by acting at GLP-1R. Subjects with diseases and/or conditions that respond favorably to GLP-1R stimulation or to the administration of GLP-1 compounds can therefore be treated with the GLP-1 fusion proteins of the present invention. These subjects are referred to as subjects "in need of treatment with GLP-1 compounds" or "in need of GLP-1R stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk of developing non-insulin dependent diabetes (see WO 00/07617). Subjects with impaired glucose tolerance or impaired fasting glucose, subjects whose body weight is about 25% above normal body weight for the subject's height and body fluid, subjects with a partial pancreatectomy, subjects having one or both parents with non-insulin dependent diabetes, subjects who have had gestational diabetes and subjects who have had acute or chronic pancreatitis are at risk of developing non-insulin dependent diabetes. An effective amount of the fusion proteins described herein is the dosage which results in a desired therapeutic and/or prophylactic effect without causing unacceptable side-effects when administrated to a subject in need of GLP-1 receptor stimulation. A "desired therapeutic effect" includes one or more of the followings: an amelioration of the symptom(s) associated with the disease or condition; a delay in the onset of symptoms associated with the disease or condition; increased longevity compared with the absence of the treatment; and better quality of life compared with that in the absence of the treatment. An "effective amount" of the GLP-1 fusion proteins for the treatment of diabetes is the amount that would result in better control of blood glucose concentration compared with that in the absence of the treatment, thereby resulting in a delay in the onset of diabetic complications such as retinopathy, neuropathy or kidney diseases. An "effective amount" of the GLP-1 fusion protein for the prevention of diabetes is the amount that would delay, compared with that in the absence of treatment, the onset of elevated blood glucose levels that requires treatment with anti-hyperglycaemic drugs such as sulfonyl urea, thiazolidinedione, insulin and/or bisguanidine. The dosage of fusion proteins effective to normalize a patient's blood glucose will depend on a number of factors, among which are included, without limitation, the subject's sex, weight and age, the severity of inability to regulate blood glucose, the route of administration and bioavailability, the pharmacokinetic profile of the fusion protein, the potency, and the formulation. Doses may be in the range of 0.01 to 1 mg/kg body weight, preferably in the range of 0.05 to 0.5 mg/kg body weight. It is preferable that the fusion proteins of the present invention are administered either once a week or twice a week. Depending on the disease to be treated, it may be necessary to administrate the fusion protein more frequently such as three or more times per week.

BRIEF DESCRIPTION OF THE FIGURES

FIG. 6 and FIG. 5 are the results of two parallel experiments.

SPECIFIC EMBODIMENTS OF THE INVENTION

Figure 1:
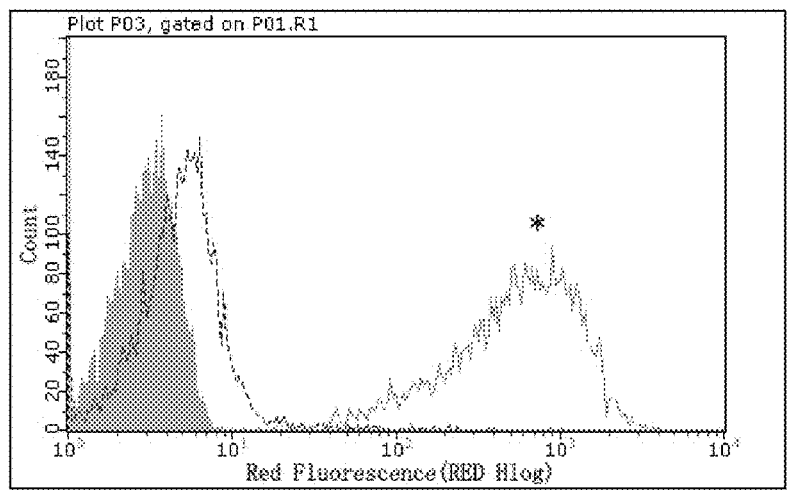
FIG. 1 is a flow cytometry (FACS) showing the specific binding of a recombinant expressed GLP-1 fusion protein (GLP-1(A8G)-LK-L13H13) with human GLP-1R (hGLP-1R) stably expressed in the Chinese hamster ovary cell line (solid line peak, marked with *) in comparison with the Chinese hamster ovary cell line itself (dotted line peak).

Through the following specific embodiments in combination with the figures, the technical solutions of the present invention are further illustrated.

In this invention, unless referred specifically, the employed raw materials, equipments and the like can all be purchased from the market or are commonly used in the art. The methods of the following embodiments, if not indicated specifically, are all conventional methods in the art.

Step 1: Construction of Stable Antigen Cell Line for Immunization

CHO-DHFR minus cells are transferred into a 6-well plate and transfected with the pYS plasmid carrying hGLP-1R gene (see SEQ ID NO: 113 for the nucleotide sequence, and see SEQ ID NO: 114 for the amino acid sequence) after 24 hr culture. The medium is changed before transfection, and it is carried out by following the recommended transfection conditions provided by the manufacturer of Lipofectamine 2000 (Invitrogen). 48 hr after transfection, the medium of the culture is replaced by the complete medium containing 10 nM MTX. The medium is changed every 3 days for about two weeks, until stable clones appear. The dispersed cell colonies are detached from the plate and collected. After cells grow to about 50% confluence, gradually increasing concentrations of MTX (up to a concentration of 10 μM MTX) are added for pressure selection. The constructed stable cell lines are tested by FACS analysis using antibodies (Abcam) against hGLP-1R to identify cell clones after pressure selection. There is a lot of hGLP-1R expression in the selected CHO-DHFR-hGLP-1R cell membranes after MTX selection. Finally six high-expression and stable cell lines of hGLP-1R are identified through subcloning.

Step 2: Preparation of Antibodies

Freund's adjuvant emulsified CHO-DHFR-hGLP-1R whole-cells are used at $2\times10^6$ cells/mouse dosage for subcutaneous injection into BALB/c mice (6-8 weeks). After 2 weeks, the immunity of the mice is boosted with incomplete Freund's adjuvant emulsified immunogen, and then once a week. The blood samples are collected from the clipped tail end and centrifuged to collect the serum for detecting the serum titers by FACS analysis. After the acceptable antibody titers are achieved, the mice are sacrificed and their spleen cells are harvested under aseptic condition. SP2/0 cells are collected at the logarithmic phase of growth with 3 min centrifugation at 2000 rpm. The precipitation is resuspended with serum-free culture medium, then centrifuged and resuspended for a second time, and counted. Spleen cells and SP2/0 cells are mixed at ratio of SP2/0 cells:spleen cells ≥1:1, followed by 3 rounds of washing-centrifugation. After the precipitation from the last centrifugation is detached, 1 ml of the PEG-1350 (pre-warmed to 37° C.) is added drop wise (finished in 30 s), after pipette-mixing for 1 min, 30 ml (pre-warmed to 37° C.) serum-free medium (Invitrogen) is added slowly to terminate the PEG fusion. After 5 min centrifugation at 1500 rpm, the cell pellets are resuspended and RPMI1640 (Invitrogen) containing HAT (sarcine, amethopterin and thymidine; Invitrogen) and 20% FBS (Bioind) is added as the fusion culture medium. 20000 spleen cells and 5000 feeder layer cells in 100 μl volume are plated into each well of 96-well plates. Fused hybridoma cells and feeder layer cells are co-cultured in 96-well plates with HAT selection to get rid of the non-fused cells. After 10 days, the supernatant of the hybridoma cells in the culture plates is collected for ELISA test.

Step 3: ELISA Screening of the Whole Cells

CHO-DHFR-hGLP-1R cells over-expressing hGLP-1R and CHO-DHFR minus cells not expressing hGLP-1R, were separately transferred into a 96-well plate, and kept growing to 90% confluent. The supernatant of the culture medium is removed and attached cells are washed twice with PBS, then 100 μl 100% methanol is added to fix the cells for 10 min at 4° C. then 100 μl freshly made 0.6% $H_2O_2$-PBS is added, and after incubation at room temperature for 20 min, the cells are washed twice with PBS. After blocking with PBS-1% BSA solution, the hybridoma supernatant is added and incubated for 90 min at 4° C. After several washes, 100 μl of the secondary antibody GxM-HRP-Fc (Sigma-Aldrich) (5000-times diluted) is added into each well and incubated at 37° C. for 0.5 hr. After washing for five times, 100 μl of TMB chromogenic substrate is added into each well and incubated at 37° C. for 15 min, and then 2M $H_2SO_4$ is added to terminate the reaction for reading of OD450 values. Positive control is the mouse serum after immunization; negative control is the cell culture supernatant. Hybridoma clones secreting anti-hGLP-1R antibody are screened and the stable secretory cell lines against hGLP-1R are obtained after cloning. Lastly, antibody supernatant secreted by hybridoma is verified by FACS analysis.

Step 4: Flow Analysis (FACS) of the Supernatant of the Positive Hybridoma Cells

PBS containing 10 mM EDTA is used to detach and collect $10^5$ CHO DHFR-hGLP-1R cells into a 1.5 ml EP tube. The supernatant is removed after centrifugation and the negative control sample is resuspended with a loading buffer (PBS, 2% FBS). For positive control, 200 μl antibody supernatant is added to resuspend the cells with incubation at room temperature; the cells are then centrifuged at 1500 rpm to remove the supernatant, washed with loading buffer and centrifuged again. The cells are resuspended with addition of FITC labeled goat anti-mouse fluorescent antibody at 1:50 dilution (BD Pharmingen, 200 μl/well) and incubated at room temperature for 30 min in the dark. Supernatant is removed after centrifugation, cells are washed with loading buffer, centrifuged again and resuspended with loading buffer for analysis. The hybridoma supernatant and CHO-DHFR-hGLP-1R cells have specific binding: gray peak and dotted line peak are negative controls; the solid line peak (marked with *), corresponding to the hybridoma supernatant, moves to the right obviously (FIG. 1).

Step 5: Cloning and Subcloning of Antibody Genes

Hybridoma cells secreting antibody are collected. Hybridoma mRNA is extracted according to the manufacturer protocol of QIAGEN mRNA extraction kit. Then the extracted mRNA is transcribed reversely into cDNA. The reverse transcription primers are specific primers for the light and heavy chain constant regions of mouse, with the heavy chain reverse transcription primer being (5'-TTTG-GRGGGAAGATGAAGAC-3') (SEQ ID NO: 115), the light chain reverse transcription primers being (5'-TTAACACTCTCCCCTGTTGAA-3') (SEQ ID NO: 116) and (5'-TTAACACTCATTCCTGTTGAA-3') (SEQ ID NO: 117). RT-PCR reaction conditions are as following: 25° C. for 5 min, 50° C. for 60 min, and 70° C. for 15 min. Reversely transcribed cDNA is diluted with 0.1 mM TE to 500 μl, added into the ultrafiltration centrifuge tube (Amicon Ultra-0.5) and centrifuged at 2000 g for 10 min. The filtrate is removed, 500 μl of 0.1 mM TE is added and centrifuged at 2000 g for 10 min. The filtrate is removed and the preparation tube is placed in inversion to the new centrifugal tube, and centrifuged at 2000 g for 10 min to obtain the purified cDNA. 10 μl of purified cDNA serves as the template. Add 4 μl 5× tailing buffer, 4 μl dATP (1 mM) and 10 U terminal transferase (Promega), mix uniformly and incubate at 37° C. for 5 min and at 65° C. for 5 min. The PolyA tail cDNA is used as templates and PCR is performed to amplify light and heavy chain variable region genes of antibodies. Upstream primers are all OligodT, with heavy chain downstream primers being (5'-TGGACAGGGATC-CAGAGTTCC-3') (SEQ ID NO: 118) and (5'-TGGACA-GGGCTCCATAGTTCC-3') (SEQ ID NO: 119), and light chain downstream primer being (5'-ACTCGTCCTTGGT-CAACGTG-3') (SEQ ID NO: 120). The PCR reaction conditions are as following: 95° C. for 5 min; 95° C. 30 s, 56° C. for 30 s, 72° C. for 1 min, 40 cycles; and 72° C. for 7 min. The PCR products are connected to the PMD 18-T vector for sequencing. The resulting sequences of the light and heavy chain variable regions of the antibody after sequencing are listed in the attached Sequence Listing.

PCR primers are designed based on the sequenced DNA sequences of the antibody, thus the complete light chain, heavy chain signal peptides and variable domains and mouse IgG1 constant region are connected with expression vector pTM5.

Step 6: Transient Expression of Anti-GLP-1R Antibodies in HEK293 Suspension Host Cell Line The suspension HEK293 or CHO expressing cell line are inoculated to a shaker flask, and after 24 hr rotation at 37° C., the cells are ready for transfection. Polyethylenimine (PEI) is used as a transfection reagent during transfection, and its mixture with DNA is added into the cell culture. The mixing optimization ratio of PEI to DNA is 1:1 to 5:1. PEI/DNA mixture treated cells is rotated for more than 96 hr at 37° C. to express the antigen binding protein, meanwhile 0.5% of tryptone is added into the cell culture as the source of amino acids required by expression, and finally the cell supernatant is collected for the purification and separation of the antigen binding protein.

Step 7: Antibody Humanization and Optimization

First of all, the sequences of light and heavy chain variable regions of the screened mouse antibody are aligned with the homologous antibodies, using NCBI online antibody variable region sequence alignment tool (Ig Blast) to search the germline gene sequences of a humanized antibody (Ig Germline Gene sequence) homologous to the selected antibodies variable region sequence for humanization, and the humanized gene sequence with highest homology except CDR sequences is used as template for CDR grafting to get the humanized antibody variable region sequences and to synthesize humanized antibody light and heavy chain genes. According to the sequence, PCR primers are designed and at the 5' end and 3' end of the synthetic sequence, appropriate restriction enzyme sites are introduced. By PCR, the humanized antibody variable regions are amplified and then combined with the human IgG2 or IgG4 constant region sequence to obtain the whole recombinant humanized antibody sequence. The expression of the recombinant antibodies is achieved according to step 6, and its affinity towards GLP-1R is verified by FACS analysis as described in step 4. The best humanized antibody candidate retaining affinity towards GLP-1R is selected from the group thereof, and by means of site-specific mutagenesis, its variable region sequence is further improved for better affinity towards GLP-1R.

Step 8: Cloning and Subcloning of Genes of the Humanized Fusion Protein of GLP-1

Optimized humanized antibody is fused with GLP-1 or its derivative sequence, at the N-terminal and C-terminal of the light chains, to form the GLP-1 fusion protein, and the sequences of the two are connected by a peptide linker sequence (LK). Nucleotide sequence of the signal peptide-GLP-1 peptide linker is synthesized by Genscript Biotechnology CO., LTD. Using the synthetic gene as the template, PCR amplifies the sequence of the part "signal peptide-GLP1-linker", with PCR upstream primer being (5'-CCAC-CATGGACTTTGGGCTGAGC-3') (SEQ ID NO: 121), PCR downstream primer being (5'-AGAGCCGGTGGCA-GAGCCAG-3') (SEQ ID NO: 122). The PCR reaction conditions are as following: 95° C. for 5 min; 95° C. for 30 s, 56° C. for 30 s, 72° C. for 30 s, 35 cycles; 72° C. for 7 min. In addition, using the nucleotide sequence of the humanized antibody as template, the sequence of the antibody part of the fusion protein sequence is amplified.

The PCR upstream primer is (5'-CTGGCTCTGCCAC-CGGCTCTGCCATCCAGATGACCCAGTCTCC-3') (SEQ ID NO: 123) and the PCR downstream primer is (5'-ACACTCTCCCCTGTTGAAGCTC-3') (SEQ ID NO: 124). The PCR reaction conditions are as following: 95° C. for 5 min; 95° C. for 30 s, 56° C. for 30 s, 72° C. for 1 min, 35 cycles; 72° C. for 7 min. Then through overlapping PCR, the part "signal peptide-GLP-1-peptide linker" of the nucleic acid sequence of the fusion protein is connected with the antibody part, introducing two restriction enzyme sites Nhe1 and Not1 to both ends of the primers, and thus complete fusion protein sequence and the expression vector pTM5 are linked together. Overlapping PCR upstream primer is (5'-CCGGCTAGCCACCATGGACTTTGGGCTGAGC-3') (SEQ ID NO: 125) and the downstream primer is (5'-AGTGCGGCCGCTCAACACTCTCCCCTGTT-GAAGCTC-3') (SEQ ID NO: 126). The PCR reaction conditions are as following: 95° C. for 5 min; 95° C. for 30 s, 56° C. for 30 s, 72° C. for 1 min, 35 cycles; 72° C. for 7 min. The PCR products are connected to the PTM5 vector and then are confirmed by sequencing.

Step 9: Transient Expression of GLP-1 Fusion Protein in HEK293 Suspension Host Cell Line HEK293 suspension cells are inoculated into a shaker flask and the culture medium is changed before transfection. The vectors containing fusion protein light/heavy chain gene at the concentration of 0.5 to 1.5 µg/ml based on the total amount of DNA are mixed with 1.5 to 7.5 µg/ml of polyethylenimine (PEI), and after standing for 15-25 minutes the mixture is added into the cell culture medium. After 24 hr, 0.5-1% of Trypton N1 is added into the cell culture medium. The supernatants containing the secreted GLP-1 fusion protein are harvested after culturing for 5-10 days.

Step 10: Stable Expression of GLP-1 Fusion Protein in CHO Suspension Host Cell Line.

CHO suspension cells are inoculated into a 6-well plate, and the transfection of the expression vector of the fusion protein is implemented by the transfection conditions in step 1. After 48 hr, 300 mg/ml of hygromycin (heavy chain) and 6 mg/ml puromycin (light chain) are added for co-selection. After apoptosis occurred in quantity (mortality rate >90%), antibiotic concentration is gradually reduced to allow the remaining cells to recover and transferred into a shaker flask for culture expansion, then the expression of the antibody in the supernatant is confirmed. Afterwards, half of antibiotic concentrations in medium is maintained to allow the stable expression of GLP-1 fusion protein of the cells.

Step 11: Purification and Preparation of GLP-1 Fusion Protein from the Cell Culture Supernatant Cells are removed from the culture after centrifugation, and the supernatant runs through G protein coupled affinity chromatography column. The expressed GLP-1 fusion protein is eluted from the chromatography column using eluent with pH around 2.5-3.5. The low pH value of the eluent is neutralized immediately with the neutralized buffer provided in the elution tube. The protein solution is collected after elution and is then dialyzed against PBS.

Figure 2:
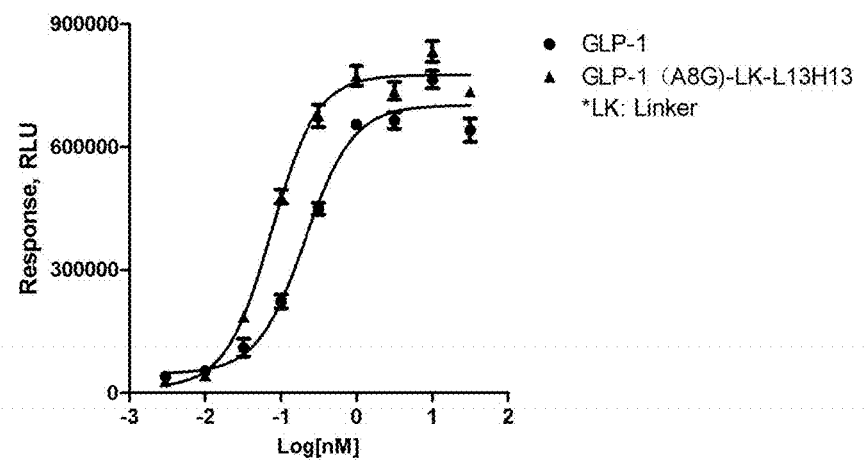
FIG. 2 shows the reporter gene assay dose-responsive curves of GLP-1 wild type (circles) and GLP-1(A8G)-LK-L13H13 (triangles) activating hGLP-1R stably expressed in Chinese hamster ovary cell line.

Step 12: Reporter Gene Assay Test of GLP-1 Fusion Protein for its Function In Vitro Activation of GLP-1R (See FIG. 2).

The CHO-DHFR minus cells co-expressing hGLP1R-CRE-Luciferase are inoculated into a 96-well cell culture plate with 20000 cells per well, and cultured at 37° C. overnight. The next day the culture supernatant is removed. The cell surfaces are washed twice with serum free medium and residual liquid is removed as well, then adding 100 µl serum free medium for dilution and purification of antibodies or GLP-1 and incubated at 37° C. for 4 hr. After the stimulation, 100 µl Bright Glo chemiluminescence substrate of Promega is added. Finally the cell lysates are transferred into a white 96-well plate, and the relative luminous intensity is recorded in SpectraMax L microplate reader of Molecular Devices.

Step 13: Glucose Tolerance Test of Fasting ICR Mice.

Figure 3:
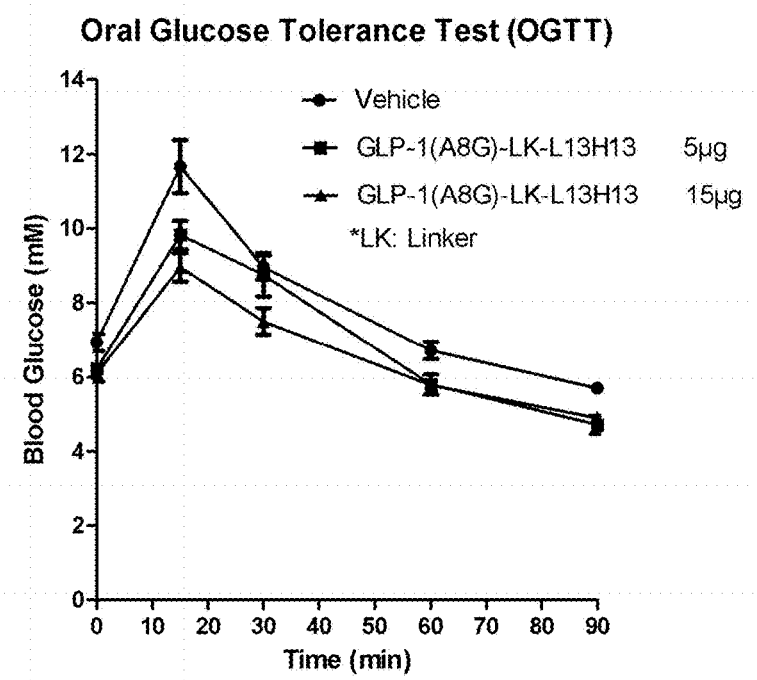
FIG. 3 is the result of a mouse (ICR) glucose tolerance test, showing the glucose tolerance of fasting mice 16 hr single i.p. injection of GLP-1(A8G)-LK-L13H13 at 5 micrograms per mouse (square) and 15 micrograms per mouse (triangles).

Glucose tolerance of mice in vein is determined to evaluate the efficacy of the GLP-1 fusion proteins (preferably, antibody GLP-1 (A8G)-LK-L13H13) disclosed in the present patent. There are four groups of mice, and each group contains at least three to five mice. Group I is the control group, received an intraperitoneal injection of same volume of PBS. Group II received a single intraperitoneal injection of 15 μg per mouse. Group III received a single intraperitoneal injection of 5 μg per mouse. After injection, mice are fasted for 6-16 hr, and after the fasting is complete, the blood samples of mice are taken to determine the basal blood glucose concentration. Then the mice are forced with a gavage of glucose at the concentration of 1.5 g/kg, and 15, 30, 60 and 90 min after the gavage, the blood samples are taken to determine blood glucose concentration, as shown in FIG. 3.

Step 14: Glucose Tolerance Test of GLP-1 Fusion Protein in Mice (C57BL) for Long-Term (40 hr) Efficacy.

Figure 4:
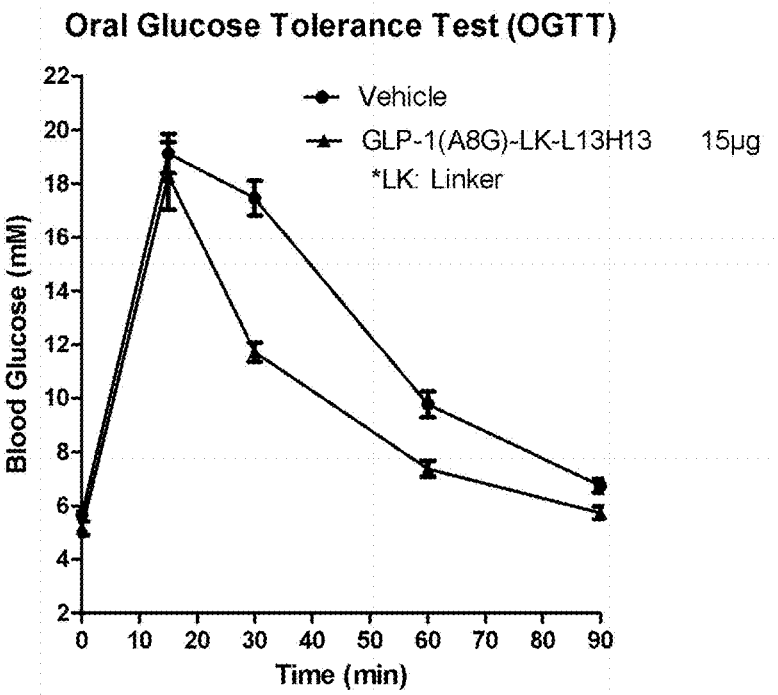
FIG. 4 is the result of a mouse (C57BL) glucose tolerance test, showing the glucose tolerance of fasting mice 40 hr single i.p. injection of GLP-1(A8G)-LK-L13H13 at 15 micrograms per mouse (triangles).

Glucose tolerance of mice in vein is determined to evaluate the long-term efficacy of the GLP-1 fusion proteins (preferably, antibody GLP-1 (A8G)-LK-L13H13) disclosed in the present patent. There are two groups of mice, and each group contains at least three to five mice. Group I is the control group, received an intraperitoneal injection of same volume of PBS. Group II received a single intraperitoneal injection of 15 μg per mouse. 24 hr after injection, mice are fasted for 16 hr, and after the fasting is complete, the blood samples of mice are taken to determine the basal blood glucose concentration. Then the mice are forced with a gavage of glucose at the concentration of 1.5 g/kg, and 15, 30, 60 and 90 min after the gavage, the blood samples are taken to determine blood glucose concentration, as shown in FIG. 4.

Step 15: Study on the Long-Term (72 hr) Effects of a GLP-1 Fusion Protein on Lowering the Blood Glucose Concentration of Type II Diabetic Mice (Db/Db Mice).

Figure 5:
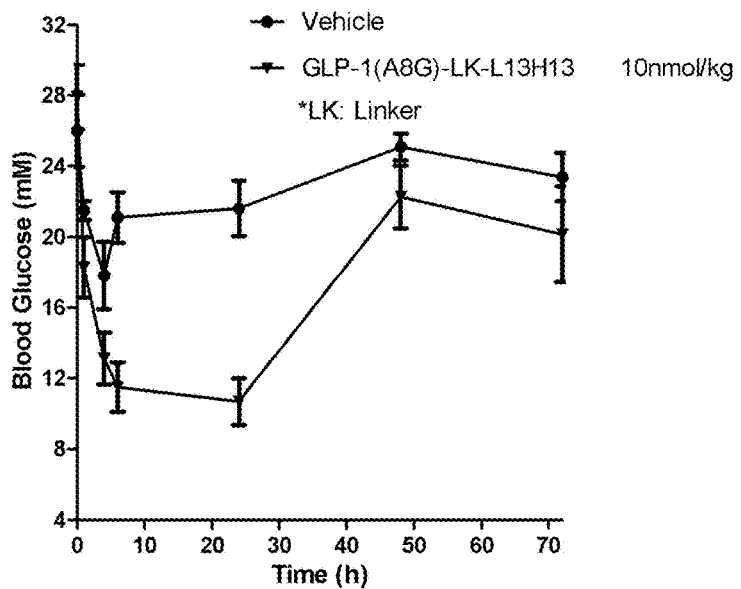
FIG. 5 is the blood glucose concentration-time curve of the type II diabetic mice (db/db mice), reflecting the blood glucose concentration change over the experiment period of the type II diabetic mice after a single i.p. injection of GLP-1(A8G)-LK-L13H13 at a concentration of 10 nmol/kg (inverted triangles).

The blood glucose concentration of type II diabetic mice are determined at different time points to evaluate the long-term efficacy of the GLP-1 fusion proteins (preferably, antibody GLP-1 (A8G)-LK-L13H13) disclosed in the present patent in lowering the blood glucose concentration of type II diabetic mice. There are two groups of mice, and each group contains at least six mice. Before the start of the injection, the blood samples of mice are taken to determine the basal blood glucose concentration. Later, Group I (the control group), received an intraperitoneal injection of same volume of PBS. Group II received a single intraperitoneal injection of the GLP-1 fusion protein at a concentration of 10 nmol/kg. 1, 4, 6, 24, 48 and 72 hr after injection, the blood samples thereof are taken respectively to determine the blood glucose concentration of the two groups of mice, as shown in FIG. 5.

Step 16: Study on the Long-Term (120 hr) Effects of a GLP-1 Fusion Protein on the Reduction of the Daily Food Intake in Type II Diabetic Mice (Db/Db Mice).

Figure 6:
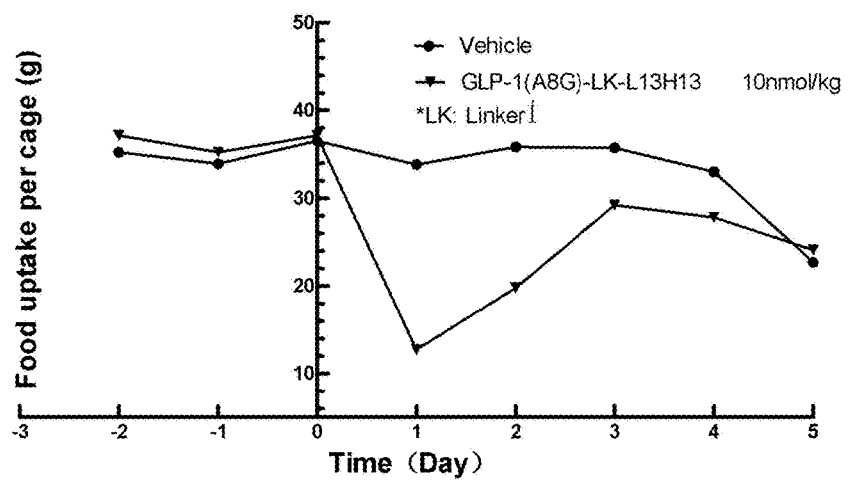
FIG. 6 is the daily food intake-time curve of the type II diabetic mice (db/db mice), reflecting the mice daily food intake change of the type II diabetic mice after i.p. injection of GLP-1(A8G)-LK-L13H13 at 10 nmol/kg (inverted triangles), during the time period from 3 days before injection of the fusion protein to 5 days after injection.

The food intake changes of type II diabetic mice are determined to evaluate the long-term efficacy of the GLP-1 fusion proteins (preferably, antibody GLP-1 (A8G)-LK-L13H13) disclosed in the present patent in reducing the food intake level of type II diabetic mice. This step is carried out along with step 15 on the same batch of mice in synchronization. There are two groups of mice, and each group contains at least six mice. From 3 days before the injection of step 15 to 5 days after injection (120 hr), every morning and at the same time, the daily food intake of each group of mice was weighed, as shown in FIG. 6.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims.

What is claimed is:

1. A method of treating non-insulin-dependent diabetes in a subject, comprising administering to the subject a therapeutically effective amount of a GLP-1 fusion protein comprising a GLP-1 and an antibody specifically binding to GLP-1R, wherein the antibody comprises: heavy chain CDR1 amino acid sequence: SEQ ID NO: 12, heavy chain CDR2 amino acid sequence: SEQ ID NO: 19, heavy chain CDR3 amino acid sequence: SEQ ID NO: 27, light chain CDR1 amino acid sequence: SEQ ID NO: 37, light chain CDR2 amino acid sequence: SEQ ID NO: 45, and light chain CDR3 amino acid sequence: SEQ ID NO: 53.

2. The method of claim 1, wherein the antibody comprises light chain variable region sequence: SEQ ID NO: 101 or SEQ ID NO: 105; and heavy chain variable region sequence: SEQ ID NO: 75 or SEQ ID NO: 79.

3. The method of claim 1, wherein the antibody comprises a light chain variable region sequence encoded by polynucleotide sequence: SEQ ID NO: 100 or SEQ ID NO: 104; and a heavy chain variable region sequence encoded by polynucleotide sequence: SEQ ID NO: 74 or SEQ ID NO: 78.

4. The method of claim 1, wherein the antibody comprises light chain variable region sequence: SEQ ID NO: 101; and heavy chain variable region sequence: SEQ ID NO: 75.

5. The method of claim 1, wherein the antibody comprises a light chain variable region sequence encoded by polynucleotide sequence: SEQ ID NO: 100; and a heavy chain variable region sequence encoded by polynucleotide sequence: SEQ ID NO: 74.

6. The method of claim 1, wherein the antibody comprises light chain variable region sequence: SEQ ID NO: 105; and heavy chain variable region sequence: SEQ ID NO: 79.

7. The method of claim 1, wherein the antibody comprises a light chain variable region sequence encoded by polynucleotide sequence: SEQ ID NO: 104; and a heavy chain variable region sequence encoded by polynucleotide sequence: SEQ ID NO: 78.

8. The method of claim 1, wherein the antibody further comprises an amino acid sequence selected from:
 (a) light chain constant region amino acid sequence: SEQ ID NO 106;
 (b) light chain constant region amino acid sequence: SEQ ID NO 107;
 (c) heavy chain constant region amino acid sequence: SEQ ID NO 108;
 (d) heavy chain constant region amino acid sequence: SEQ ID NO 109;
 (e) light chain constant region amino acid sequence: SEQ ID NO 106 and heavy chain constant region amino acid sequence: SEQ ID NO 108;
 (f) light chain constant region amino acid sequence: SEQ ID NO 107 and heavy chain constant region amino acid sequence: SEQ ID NO 108;
 (g) light chain constant region amino acid sequence: SEQ ID NO 106 and heavy chain constant region amino acid sequence: SEQ ID NO 109; and
 (h) light chain constant region amino acid sequence: SEQ ID NO 107 and heavy chain constant region amino acid sequence: SEQ ID NO 109.

9. The method of claim 1, wherein the antibody is a humanized antibody.

10. The method of claim 1, wherein the GLP-1 comprises an amino acid sequence selected from SEQ ID NO: 1, SEQ ID NO: 2, SEQ ID NO: 3, SEQ ID NO: 4, SEQ ID NO: 5, and SEQ ID NO: 127.

11. The method of claim 1, wherein the GLP-1 comprises amino acid sequence SEQ ID NO: 3, SEQ ID NO: 4, or SEQ ID NO: 5.

12. The method of claim 1, wherein the GLP-1 comprises amino acid sequence SEQ ID NO: 5.

13. The method of claim 1, wherein the GLP-1 is fused with a light chain of the antibody via a peptide linker.

14. The method of claim 13, wherein the peptide linker comprises amino acid sequence SEQ ID NO: 110, SEQ ID NO: 111, or SEQ ID NO: 112.

15. The method of claim 1, wherein the GLP-1 is fused with the light chain and/or heavy chain of the antibody in the form of N'—R1-L-R2-C', N'—R2-L-R1-C' or N'—R2-R1r-C',
 wherein:
  L is a peptide linker, comprising a full-length, partial, or repeated amino acid sequence selected from SEQ ID NO: 110, SEQ ID NO: 111, and SEQ ID NO: 112;
  R1 is an amino acid sequence of GLP-1;
  R1r is a reverse amino acid sequence of GLP-1;
  R2 is an amino acid sequence of the light chain or heavy chain of the antibody;
  C' represents a carboxyl residual terminal of the GLP-1 fusion protein polypeptide; and
  N' represents an amino residual terminal of the GLP-1 fusion protein polypeptide.

16. A method of treating obesity in a subject, comprising administering to the subject a therapeutically effective amount of a GLP-1 fusion protein comprising a GLP-1 and an antibody specifically binding to GLP-1R, wherein the antibody comprises: heavy chain CDR1 amino acid sequence: SEQ ID NO: 12, heavy chain CDR2 amino acid sequence: SEQ ID NO: 19, heavy chain CDR3 amino acid sequence: SEQ ID NO: 27, light chain CDR1 amino acid sequence: SEQ ID NO: 37, light chain CDR2 amino acid sequence: SEQ ID NO: 45, and light chain CDR3 amino acid sequence: SEQ ID NO: 53.

17. A method of treating overweight in a subject, comprising administering to the subject a therapeutically effective amount of a GLP-1 fusion protein comprising a GLP-1 and an antibody specifically binding to GLP-1R, wherein the antibody comprises: heavy chain CDR1 amino acid sequence: SEQ ID NO: 12, heavy chain CDR2 amino acid sequence: SEQ ID NO: 19, heavy chain CDR3 amino acid sequence: SEQ ID NO: 27, light chain CDR1 amino acid sequence: SEQ ID NO: 37, light chain CDR2 amino acid sequence: SEQ ID NO: 45, and light chain CDR3 amino acid sequence: SEQ ID NO: 53.

18. The method of claim 16, wherein the antibody comprises light chain variable region sequence: SEQ ID NO: 101 or SEQ ID NO: 105; and heavy chain variable region sequence: SEQ ID NO: 75 or SEQ ID NO: 79.

19. The method of claim 16, wherein the antibody comprises a light chain variable region sequence encoded by polynucleotide sequence: SEQ ID NO: 100 or SEQ ID NO: 104; and a heavy chain variable region sequence encoded by polynucleotide sequence: SEQ ID NO: 74 or SEQ ID NO: 78.

20. The method of claim 16, wherein the antibody comprises light chain variable region sequence: SEQ ID NO: 101; and heavy chain variable region sequence: SEQ ID NO: 75.

21. The method of claim 16, wherein the antibody comprises a light chain variable region sequence encoded by polynucleotide sequence: SEQ ID NO: 100; and a heavy chain variable region sequence encoded by polynucleotide sequence: SEQ ID NO: 74.

22. The method of claim 16, wherein the antibody comprises light chain variable region sequence: SEQ ID NO: 105; and heavy chain variable region sequence: SEQ ID NO: 79.

23. The method of claim 16, wherein the antibody comprises a light chain variable region sequence encoded by polynucleotide sequence: SEQ ID NO: 104; and a heavy chain variable region sequence encoded by polynucleotide sequence: SEQ ID NO: 78.

24. The method of claim 16, wherein the antibody further comprises an amino acid sequence selected from:
   (a) light chain constant region amino acid sequence: SEQ ID NO 106;
   (b) light chain constant region amino acid sequence: SEQ ID NO 107;
   (c) heavy chain constant region amino acid sequence: SEQ ID NO 108;
   (d) heavy chain constant region amino acid sequence: SEQ ID NO 109;
   (e) light chain constant region amino acid sequence: SEQ ID NO 106 and heavy chain constant region amino acid sequence: SEQ ID NO 108;
   (f) light chain constant region amino acid sequence: SEQ ID NO 107 and heavy chain constant region amino acid sequence: SEQ ID NO 108;
   (g) light chain constant region amino acid sequence: SEQ ID NO 106 and heavy chain constant region amino acid sequence: SEQ ID NO 109; and
   (h) light chain constant region amino acid sequence: SEQ ID NO 107 and heavy chain constant region amino acid sequence: SEQ ID NO 109.

25. The method of claim 16, wherein the antibody is a humanized antibody.

26. The method of claim 16, wherein the GLP-1 comprises an amino acid sequence selected from SEQ ID NO: 1, SEQ ID NO: 2, SEQ ID NO: 3, SEQ ID NO: 4, SEQ ID NO: 5, and SEQ ID NO: 127.

27. The method of claim 16, wherein the GLP-1 comprises amino acid sequence SEQ ID NO: 3, SEQ ID NO: 4, or SEQ ID NO: 5.

28. The method of claim 16, wherein the GLP-1 comprises amino acid sequence SEQ ID NO: 5.

29. The method of claim 16, wherein the GLP-1 is fused with a light chain of the antibody via a peptide linker.

30. The method of claim 29, wherein the peptide linker comprises amino acid sequence SEQ ID NO: 110, SEQ ID NO: 111, or SEQ ID NO: 112.

31. The method of claim 16, wherein the GLP-1 is fused with the light chain and/or heavy chain of the antibody in the form of N'-R1-L-R2-C', N'-R2-L-R1-C' or N'-R2-R1r-C', wherein:
   L is a peptide linker, comprising a full-length, partial, or repeated amino acid sequence selected from SEQ ID NO: 110, SEQ ID NO: 111, and SEQ ID NO: 112;
   R1 is an amino acid sequence of GLP-1;
   R1r is a reverse amino acid sequence of GLP-1;
   R2 is an amino acid sequence of the light chain or heavy chain of the antibody;
   C' represents a carboxyl residual terminal of the GLP-1 fusion protein polypeptide; and
   N' represents an amino residual terminal of the GLP-1 fusion protein polypeptide.

\* \* \* \* \*

SEQUENCE LISTING

```
<160> NUMBER OF SEQ ID NOS: 127

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Homo sapiens

<400> SEQUENCE: 2

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 3
<211> LENGTH: 22
<212> TYPE: PRT
<213> ORGANISM: Homo sapiens

<400> SEQUENCE: 3

His Gly Glu Gly Thr Phe Thr Ser Asp Val Ser Ser Tyr Leu Glu Gly
1               5                   10                  15

Gln Ala Ala Lys Glu Phe
            20

<210> SEQ ID NO 4
<211> LENGTH: 23
<212> TYPE: PRT
<213> ORGANISM: Homo sapiens

<400> SEQUENCE: 4

His Gly Glu Gly Thr Phe Thr Ser Asp Val Ser Ser Tyr Leu Glu Gly
1               5                   10                  15

Gln Ala Ala Lys Glu Phe Ile
            20

<210> SEQ ID NO 5
<211> LENGTH: 24
<212> TYPE: PRT
<213> ORGANISM: Homo sapiens

<400> SEQUENCE: 5

His Gly Glu Gly Thr Phe Thr Ser Asp Val Ser Ser Tyr Leu Glu Gly
1               5                   10                  15

Gln Ala Ala Lys Glu Phe Ile Ala
            20

<210> SEQ ID NO 6
<211> LENGTH: 10
<212> TYPE: PRT
<213> ORGANISM: Mus musculus

<400> SEQUENCE: 6

Gly Phe Ser Leu Thr Gly Tyr Gly Val Asn
1               5                   10

<210> SEQ ID NO 7
<211> LENGTH: 10
<212> TYPE: PRT
<213> ORGANISM: Mus musculus

<400> SEQUENCE: 7

Gly Phe Thr Phe Ser Asp Asn Gly Met Ala
1               5                   10

<210> SEQ ID NO 8
<211> LENGTH: 10
<212> TYPE: PRT
<213> ORGANISM: Mus musculus

<400> SEQUENCE: 8

Gly Phe Thr Phe Ser Asp Tyr Gly Met Ala
1               5                   10

<210> SEQ ID NO 9
<211> LENGTH: 10
<212> TYPE: PRT

<213> ORGANISM: Mus musculus

<400> SEQUENCE: 9

Gly Tyr Lys Phe Thr Asp Tyr Ala Met Tyr
1               5                   10

<210> SEQ ID NO 10
<211> LENGTH: 10
<212> TYPE: PRT
<213> ORGANISM: Mus musculus

<400> SEQUENCE: 10

Gly Tyr Lys Phe Thr Asp Tyr Ala Met His
1               5                   10

<210> SEQ ID NO 11
<211> LENGTH: 12
<212> TYPE: PRT
<213> ORGANISM: Mus musculus

<400> SEQUENCE: 11

Gly Phe Ser Leu Ser Thr Phe Gly Met Gly Val Gly
1               5                   10

<210> SEQ ID NO 12
<211> LENGTH: 10
<212> TYPE: PRT
<213> ORGANISM: Mus musculus

<400> SEQUENCE: 12

Gly Phe Thr Leu Ser Ser Tyr Gly Met His
1               5                   10

<210> SEQ ID NO 13
<211> LENGTH: 17
<212> TYPE: PRT
<213> ORGANISM: Mus musculus

<400> SEQUENCE: 13

Gly Met Ile Trp Gly Gly Ser Thr Asp Tyr Asn Ser Ala Leu Lys
1               5                   10                  15
Ser

<210> SEQ ID NO 14
<211> LENGTH: 17
<212> TYPE: PRT
<213> ORGANISM: Mus musculus

<400> SEQUENCE: 14

Phe Ile Ser Asn Leu Ser Tyr Arg Ile Tyr Tyr Ala Asp Thr Val Thr
1               5                   10                  15
Gly

<210> SEQ ID NO 15
<211> LENGTH: 17
<212> TYPE: PRT
<213> ORGANISM: Mus musculus

<400> SEQUENCE: 15

Phe Ile Ser Asn Leu Ala Tyr Arg Ile Tyr Tyr Ala Asp Thr Val Thr
1               5                   10                  15
Gly

<210> SEQ ID NO 16
<211> LENGTH: 17
<212> TYPE: PRT
<213> ORGANISM: Mus musculus

<400> SEQUENCE: 16

Val Ile Ser Ile Tyr Tyr Gly Asn Thr Asn Tyr Asn Gln Lys Phe Lys
1               5                   10                  15
Asp

<210> SEQ ID NO 17
<211> LENGTH: 17
<212> TYPE: PRT
<213> ORGANISM: Mus musculus

<400> SEQUENCE: 17

Val Ile Asn Ile Tyr Tyr Gly Asn Thr Ser Tyr Asn Gln Lys Phe Lys
1               5                   10                  15
Gly

<210> SEQ ID NO 18
<211> LENGTH: 16
<212> TYPE: PRT
<213> ORGANISM: Mus musculus

<400> SEQUENCE: 18

His Ile Trp Trp Asp Asp Lys Tyr Tyr Asn Pro Ala Leu Lys Ser
1               5                   10                  15

<210> SEQ ID NO 19
<211> LENGTH: 17
<212> TYPE: PRT
<213> ORGANISM: Mus musculus

<400> SEQUENCE: 19

Val Ile Trp Tyr Asp Gly Ser Asn Lys Tyr Tyr Ala Asp Ser Val Lys
1               5                   10                  15
Gly

<210> SEQ ID NO 20
<211> LENGTH: 6
<212> TYPE: PRT
<213> ORGANISM: Mus musculus

<400> SEQUENCE: 20

Gly Leu Pro Gly Asp Tyr
1               5

<210> SEQ ID NO 21
<211> LENGTH: 11
<212> TYPE: PRT
<213> ORGANISM: Mus musculus

<400> SEQUENCE: 21

Gly Thr Met Ala Pro Asn Trp Tyr Phe Asp Val
1               5                   10

<210> SEQ ID NO 22
<211> LENGTH: 11
<212> TYPE: PRT
<213> ORGANISM: Mus musculus

<400> SEQUENCE: 22

Gly Thr Thr Ala Pro Asn Trp Tyr Phe Asp Val
1               5                   10

<210> SEQ ID NO 23
<211> LENGTH: 9
<212> TYPE: PRT
<213> ORGANISM: Mus musculus

<400> SEQUENCE: 23

Gly Ile Thr Thr Ala Ala Phe Asp Tyr
1               5

<210> SEQ ID NO 24
<211> LENGTH: 9
<212> TYPE: PRT
<213> ORGANISM: Mus musculus

<400> SEQUENCE: 24

Gly Ile Thr Met Ala Ala Phe Asp Tyr
1               5

<210> SEQ ID NO 25
<211> LENGTH: 9
<212> TYPE: PRT
<213> ORGANISM: Mus musculus

<400> SEQUENCE: 25

Gly Val Thr Phe Tyr Ala Met Asp His
1               5

<210> SEQ ID NO 26
<211> LENGTH: 9
<212> TYPE: PRT
<213> ORGANISM: Mus musculus

<400> SEQUENCE: 26

Lys Gly Asn Phe Ala Trp Phe Thr Tyr
1               5

<210> SEQ ID NO 27
<211> LENGTH: 16
<212> TYPE: PRT
<213> ORGANISM: Mus musculus

<400> SEQUENCE: 27

Gly Gly Gly Ser Gly Ser Tyr Arg Tyr Tyr Tyr Gly Leu Asp Val
1               5                   10                  15

<210> SEQ ID NO 28
<211> LENGTH: 16
<212> TYPE: PRT
<213> ORGANISM: Mus musculus

<400> SEQUENCE: 28

Lys Ser Thr Lys Ser Leu Leu Asn Ser Asp Gly Phe Thr Tyr Leu Asp
1               5                   10                  15

<210> SEQ ID NO 29
<211> LENGTH: 10
<212> TYPE: PRT
<213> ORGANISM: Mus musculus

<400> SEQUENCE: 29

Arg Ala Ser Ser Ser Val Thr Tyr Ile His

-continued

```
<210> SEQ ID NO 30
<211> LENGTH: 10
<212> TYPE: PRT
<213> ORGANISM: Mus musculus

<400> SEQUENCE: 30

Arg Ala Ser Ser Ser Val Ser Tyr Met Tyr
1               5                   10

<210> SEQ ID NO 31
<211> LENGTH: 8
<212> TYPE: PRT
<213> ORGANISM: Mus musculus

<400> SEQUENCE: 31

Gln Gly Ile Ser Asn Tyr Leu Asn
1               5

<210> SEQ ID NO 32
<211> LENGTH: 17
<212> TYPE: PRT
<213> ORGANISM: Mus musculus

<400> SEQUENCE: 32

Lys Ser Ser Gln Ser Leu Leu Asn Ser Gly Asn Gln Lys Asn Tyr Leu
1               5                   10                  15

Ala

<210> SEQ ID NO 33
<211> LENGTH: 10
<212> TYPE: PRT
<213> ORGANISM: Mus musculus

<400> SEQUENCE: 33

Arg Ala Ser Ser Ser Val Thr Tyr Ile His
1               5                   10

<210> SEQ ID NO 34
<211> LENGTH: 16
<212> TYPE: PRT
<213> ORGANISM: Mus musculus

<400> SEQUENCE: 34

Arg Ser Ser Lys Ser Leu Leu Asp Arg Asn Gly Asn Thr Tyr Leu Tyr
1               5                   10                  15

<210> SEQ ID NO 35
<211> LENGTH: 16
<212> TYPE: PRT
<213> ORGANISM: Mouse

<400> SEQUENCE: 35

Arg Ser Ser Lys Ser Leu Leu His Ser Asn Gly Asn Thr Tyr Leu Tyr
1               5                   10                  15

<210> SEQ ID NO 36
<211> LENGTH: 17
<212> TYPE: PRT
<213> ORGANISM: Mus musculus

<400> SEQUENCE: 36

Lys Ser Ser Gln Ser Leu Leu Asn Ser Ser Asn Gln Lys Asn Tyr Leu
```

Ala

<210> SEQ ID NO 37
<211> LENGTH: 11
<212> TYPE: PRT
<213> ORGANISM: Mus musculus

<400> SEQUENCE: 37

Arg Ala Ser Gln Asn Ile Asn Asn Leu Leu Ala
1               5                   10

<210> SEQ ID NO 38
<211> LENGTH: 7
<212> TYPE: PRT
<213> ORGANISM: Mus musculus

<400> SEQUENCE: 38

Leu Val Ser Asn Arg Phe Ser
1               5

<210> SEQ ID NO 39
<211> LENGTH: 7
<212> TYPE: PRT
<213> ORGANISM: Mus musculus

<400> SEQUENCE: 39

Gly Thr Ser Asn Leu Ala Ser
1               5

<210> SEQ ID NO 40
<211> LENGTH: 7
<212> TYPE: PRT
<213> ORGANISM: Mus musculus

<400> SEQUENCE: 40

Ala Thr Ser Asn Leu Ala Ser
1               5

<210> SEQ ID NO 41
<211> LENGTH: 7
<212> TYPE: PRT
<213> ORGANISM: Mus musculus

<400> SEQUENCE: 41

Tyr Thr Ser Ser Leu His Ser
1               5

<210> SEQ ID NO 42
<211> LENGTH: 7
<212> TYPE: PRT
<213> ORGANISM: Mus musculus

<400> SEQUENCE: 42

Gly Ala Ser Thr Arg Glu Ser
1               5

<210> SEQ ID NO 43
<211> LENGTH: 7
<212> TYPE: PRT
<213> ORGANISM: Mus musculus

<400> SEQUENCE: 43

Arg Met Ser Asn Leu Ala Ser

```
<210> SEQ ID NO 44
<211> LENGTH: 7
<212> TYPE: PRT
<213> ORGANISM: Mus musculus

<400> SEQUENCE: 44

Phe Ala Ser Thr Arg Glu Ser
1               5

<210> SEQ ID NO 45
<211> LENGTH: 7
<212> TYPE: PRT
<213> ORGANISM: Mus musculus

<400> SEQUENCE: 45

Thr Ala Ser Ser Leu Gln Ser
1               5

<210> SEQ ID NO 46
<211> LENGTH: 9
<212> TYPE: PRT
<213> ORGANISM: Mus musculus

<400> SEQUENCE: 46

Phe Gln Ser Asn Tyr Leu Pro Phe Thr
1               5

<210> SEQ ID NO 47
<211> LENGTH: 9
<212> TYPE: PRT
<213> ORGANISM: Mus musculus

<400> SEQUENCE: 47

Gln Gln Trp Ser Ser Asn Pro Pro Thr
1               5

<210> SEQ ID NO 48
<211> LENGTH: 9
<212> TYPE: PRT
<213> ORGANISM: Mus musculus

<400> SEQUENCE: 48

Gln Gln Trp Thr Ser Asn Pro Pro Thr
1               5

<210> SEQ ID NO 49
<211> LENGTH: 9
<212> TYPE: PRT
<213> ORGANISM: Mus musculus

<400> SEQUENCE: 49

Gln Gln Tyr Ser Lys Leu Pro Tyr Thr
1               5

<210> SEQ ID NO 50
<211> LENGTH: 9
<212> TYPE: PRT
<213> ORGANISM: Mus musculus

<400> SEQUENCE: 50

Gln Asn Asp His Ser Tyr Pro Phe Thr
1               5
```

<210> SEQ ID NO 51
<211> LENGTH: 9
<212> TYPE: PRT
<213> ORGANISM: Mus musculus

<400> SEQUENCE: 51

Met Gln His Leu Glu Tyr Pro Tyr Thr
1               5

<210> SEQ ID NO 52
<211> LENGTH: 9
<212> TYPE: PRT
<213> ORGANISM: Mus musculus

<400> SEQUENCE: 52

Gln Gln His Tyr Tyr Thr Pro Tyr Thr
1               5

<210> SEQ ID NO 53
<211> LENGTH: 9
<212> TYPE: PRT
<213> ORGANISM: Mouse

<400> SEQUENCE: 53

Gln Gln Ala His Arg Phe Pro Pro Thr
1               5

<210> SEQ ID NO 54
<211> LENGTH: 342
<212> TYPE: DNA
<213> ORGANISM: Mus musculus

<400> SEQUENCE: 54
caggtgcaac tgaaggagtc aggacctggc ctggtggcgc cctcacagag cctgtccatc       60
acatgcaccg tctcaggatt ctcattaacc ggctatggtg taaactgggt tcgccagcct      120
ccaggaaagg gtctggagtg gctgggaatg atatggggtg gtggaagcac agactataat      180
tcagctctca atccagact gagcatcagc aaggacaact ccaagagcca agttttctta      240
aaaatgaaca gtctgcaaag tgatgacaca gccaggtact actgtgccag aggactaccg      300
ggggactact ggggtcgagg aacctcagtc accgtctcct ca                         342

<210> SEQ ID NO 55
<211> LENGTH: 114
<212> TYPE: PRT
<213> ORGANISM: Mus musculus

<400> SEQUENCE: 55

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ser Asp Asp Thr Ala Arg Tyr Tyr Cys Ala
                85                  90                  95

Arg Gly Leu Pro Gly Asp Tyr Trp Gly Arg Gly Thr Ser Val Thr Val
            100                 105                 110

Ser Ser

<210> SEQ ID NO 56
<211> LENGTH: 360
<212> TYPE: DNA
<213> ORGANISM: Mus musculus

<400> SEQUENCE: 56
gaggtgaagc tggtggagtc tgggggcggc atagtgcagc ctggagggtc ccggaaactc      60
tcctgtgcag cctctggatt cactttcagt gacaacggaa tggcgtgggt tcgacaggct     120
ccagggaagg ggcctgagtg ggtagcattc attagtaatt tgtcatatag gatctactat     180
gcagacactg tgacgggccg attcaccgtc tctagagaga tgccaagaa caccctgtac     240 ctggaaatga gcagtctgcg gtctgaggac acagccttt actactgtgc acggggcact     300
atggctccta actggtactt cgatgtctgg ggcgcaggga ccacggtcac cgtctcctca     360

<210> SEQ ID NO 57
<211> LENGTH: 120
<212> TYPE: PRT
<213> ORGANISM: Mus musculus

<400> SEQUENCE: 57

Glu Val Lys Leu Val Glu Ser Gly Gly Gly Ile Val Gln Pro Gly Gly
1               5                   10                  15

Ser Arg Lys Leu Ser Cys Ala Ala Ser Gly Phe Thr Phe Ser Asp Asn
            20                  25                  30

Gly Met Ala Trp Val Arg Gln Ala Pro Gly Lys Gly Pro Glu Trp Val
        35                  40                  45

Ala Phe Ile Ser Asn Leu Ser Tyr Arg Ile Tyr Tyr Ala Asp Thr Val
    50                  55                  60

Thr Gly Arg Phe Thr Val Ser Arg Glu Asn Ala Lys Asn Thr Leu Tyr
65                  70                  75                  80

Leu Glu Met Ser Ser Leu Arg Ser Glu Asp Thr Ala Phe Tyr Tyr Cys
                85                  90                  95

Ala Arg Gly Thr Met Ala Pro Asn Trp Tyr Phe Asp Val Trp Gly Ala
            100                 105                 110

Gly Thr Thr Val Thr Val Ser Ser
        115                 120

<210> SEQ ID NO 58
<211> LENGTH: 360
<212> TYPE: DNA
<213> ORGANISM: Mus musculus

<400> SEQUENCE: 58
gaggtgaagg tggtggagtc tgggggaggc ttagtgcagc ctggagggtc ccggaaactc      60
tcctgtgcag cctctggatt cactttcagt gactacggaa tggcgtgggt tcgacaggct     120
ccagggaagg ggcctgagtg ggtagcattc attagtaatt tggcatatag aatctactat     180
gcagacactg tgacgggccg attcaccatc tctagagaga tgccaagaa caccctgtac     240 ctggaaatga gcagtctgag gtctgaggac acagccatgt attactgtgc aaggggcact     300
acggctccta actggtactt cgatgtctgg ggcgcaggga ccacggtcac cgtctcctca     360

<210> SEQ ID NO 59

```
<211> LENGTH: 120
<212> TYPE: PRT
<213> ORGANISM: Mus musculus

<400> SEQUENCE: 59
```

| | | | | | | | | | | | | | | |
|---|---|---|---|---|---|---|---|---|---|---|---|---|---|---|
| Glu | Val | Lys | Val | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |

Ser Arg Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Trp Val
         35                  40                  45

Ala Phe Ile Ser Asn Leu Ala Tyr Arg Ile Tyr Tyr Ala Asp Thr Val
     50                  55                  60

Thr Gly Arg Phe Thr Ile Ser Arg Glu Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Ala Arg Gly Thr Thr Ala Pro Asn Trp Tyr Phe Asp Val Trp Gly Ala
            100                 105                 110

Gly Thr Thr Val Thr Val Ser Ser
            115                 120

```
<210> SEQ ID NO 60
<211> LENGTH: 354
<212> TYPE: DNA
<213> ORGANISM: Mus musculus

<400> SEQUENCE: 60
```

```
caggtccagc tgcagcagtc tgggcctgag ctggtgaggc ctggggtctc agtgaagatt      60
tcctgcaagg gttccggcta caaattcact gattatgcta tgtactgggt gaagcagagt     120
catgcaaaga gtctagagtg gattggagtt attagtattt actatggtaa tacaaactac     180
aaccagaagt ttaaggacaa ggccacaatg actgtagaca atcctccag cacagcctat      240
atggaacttg ccagattgac atctgaggat tctgccatct attactgtgc aaggggggatt     300
actacggccg cttttgacta ctggggccaa ggcaccactc tcacagtctc ctca            354
```

```
<210> SEQ ID NO 61
<211> LENGTH: 118
<212> TYPE: PRT
<213> ORGANISM: Mus musculus

<400> SEQUENCE: 61
```

Gln Val Gln Leu Gln Gln Ser Gly Pro Glu Leu Val Arg Pro Gly Val
 1               5                  10                  15

Ser Val Lys Ile Ser Cys Lys Gly Ser Gly Tyr Lys Phe Thr Asp Tyr
            20                  25                  30

Ala Met Tyr Trp Val Lys Gln Ser His Ala Lys Ser Leu Glu Trp Ile
         35                  40                  45

Gly Val Ile Ser Ile Tyr Tyr Gly Asn Thr Asn Tyr Asn Gln Lys Phe
     50                  55                  60

Lys Asp Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Gly Ile Thr Thr Ala Ala Phe Asp Tyr Trp Gly Gln Gly Thr
            100                 105                 110

Thr Leu Thr Val Ser Ser
        115

<210> SEQ ID NO 62
<211> LENGTH: 354
<212> TYPE: DNA
<213> ORGANISM: Mus musculus

<400> SEQUENCE: 62
caggtccagc tgcagcagtc tgggcctgag ctggtgaggc ctggggtctc agtgaagatt      60
tcctgcaagg gttccggcta caaattcact gattatgcta tgtattgggt gaagcagagt     120
catgcaaaga gtctagagtg gattggagtt attagtattt attatggtaa tacaaactac     180
aaccagaagt ttaagggcaa ggccacaatg actgtagaca atcctccaa cacagcctat      240 atggaacttg ccagattgac atctgaggat tctgccatct attactgtgc aaggggatt      300 actatggccg cttttgacta ctggggccaa ggcaccactc tcacagtctc ctca           354

<210> SEQ ID NO 63
<211> LENGTH: 118
<212> TYPE: PRT
<213> ORGANISM: Mus musculus

<400> SEQUENCE: 63

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Lys Phe Thr Asp Tyr
                20                  25                  30

Ala Met Tyr Trp Val Lys Gln Ser His Ala Lys Ser Leu Glu Trp Ile
            35                  40                  45

Gly Val Ile Ser Ile Tyr Tyr Gly Asn Thr Asn Tyr Asn Gln Lys Phe
        50                  55                  60

Lys Gly Lys Ala Thr Met Thr Val Asp Lys Ser Ser Asn Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Ile Thr Met Ala Ala Phe Asp Tyr Trp Gly Gln Gly Thr
            100                 105                 110

Thr Leu Thr Val Ser Ser
        115

<210> SEQ ID NO 64
<211> LENGTH: 360
<212> TYPE: DNA
<213> ORGANISM: Mus musculus

<400> SEQUENCE: 64
gaggtgaagc tggtggagtc tgggggcggc atagtgcagc ctggagggtc ccggaaactc      60
tcctgtgcag cctctggatt cactttcagt gacaacggaa tggcgtgggt tcgacaggct    120
ccagggaagg ggcctgagtg ggtagcattc attagtaatt tgtcatatag gatctactat    180
gcagacactg tgacgggccg attcaccgtc tctagagaga tgccaagaa cacccctgtac    240 ctggaaatga gcagtctgcg gtctgaggac acagcctttt actactgtgc acggggcact    300
atggctccta actggtactt cgatgtctgg ggcgcaggga ccacggtcac cgtctcctca    360

<210> SEQ ID NO 65
<211> LENGTH: 120
<212> TYPE: PRT

<213> ORGANISM: Mus musculus

<400> SEQUENCE: 65

| Glu | Val | Lys | Leu | Val | Glu | Ser | Gly | Gly | Gly | Ile | Val | Gln | Pro | Gly | Gly |
|---|---|---|---|---|---|---|---|---|---|---|---|---|---|---|---|
| 1 | | | | 5 | | | | | 10 | | | | | 15 | |

Ser Arg Lys Leu Ser Cys Ala Ala Ser Gly Phe Thr Phe Ser Asp Asn
          20               25              30

Gly Met Ala Trp Val Arg Gln Ala Pro Gly Lys Gly Pro Glu Trp Val
        35                40              45

Ala Phe Ile Ser Asn Leu Ser Tyr Arg Ile Tyr Tyr Ala Asp Thr Val
  50                55              60

Thr Gly Arg Phe Thr Val Ser Arg Glu Asn Ala Lys Asn Thr Leu Tyr
65               70              75             80

Leu Glu Met Ser Ser Leu Arg Ser Glu Asp Thr Ala Phe Tyr Tyr Cys
        85                90              95

Ala Arg Gly Thr Met Ala Pro Asn Trp Tyr Phe Asp Val Trp Gly Ala
          100            105           110

Gly Thr Thr Val Thr Val Ser Ser
          115            120

<210> SEQ ID NO 66
<211> LENGTH: 354
<212> TYPE: DNA
<213> ORGANISM: Mus musculus

<400> SEQUENCE: 66

```
caggtccagc tgcagcagtc tggggctgag atggtgaggc ctggggtctc agtgaagatt      60
tcctgcaagg gttctggcta caaattcact gattacgcta tgcactgggt gaagcagagt     120
catgcaaaga gtctagagtg gattggagtt attaatattt attatggtaa taccagttac     180
aaccagaagt tcaagggcaa ggccacaatg actattgaca gatcctccag cacagcctat     240
atggaacttg ccagactgac atctgacgat tctgccatct attattgtgc aagaggggtt     300
accttttatg ctatggacca ctggggtcaa ggaacctcag tcaccgtctc ctca           354
```

<210> SEQ ID NO 67
<211> LENGTH: 118
<212> TYPE: PRT
<213> ORGANISM: Mus musculus

<400> SEQUENCE: 67

Gln Val Gln Leu Gln Gln Ser Gly Ala Glu Met Val Arg Pro Gly Val
1                5                  10              15

Ser Val Lys Ile Ser Cys Lys Gly Ser Gly Tyr Lys Phe Thr Asp Tyr
          20               25              30

Ala Met His Trp Val Lys Gln Ser His Ala Lys Ser Leu Glu Trp Ile
        35                40              45

Gly Val Ile Asn Ile Tyr Tyr Gly Asn Thr Ser Tyr Asn Gln Lys Phe
  50                55              60

Lys Gly Lys Ala Thr Met Thr Ile Asp Arg Ser Ser Ser Thr Ala Tyr
65               70              75             80

Met Glu Leu Ala Arg Leu Thr Ser Asp Asp Ser Ala Ile Tyr Tyr Cys
        85                90              95

Ala Arg Gly Val Thr Phe Tyr Ala Met Asp His Trp Gly Gln Gly Thr
          100            105           110

Ser Val Thr Val Ser Ser
          115

<210> SEQ ID NO 68
<211> LENGTH: 354
<212> TYPE: DNA
<213> ORGANISM: Mus musculus

<400> SEQUENCE: 68

```
caggtccagc tgcagcagtc tgggcctgag ctggtgaggc ctggggtctc agtgaagatt      60
tcctgcaagg gttccggcta caaattcact gattatgcta tgtattgggt gaagcagagt     120
catgcaaaga gtctagagtg gattggagtt attagtattt attatggtaa tacaaactac     180
aaccagaagt ttaagggcaa ggccacaatg actgtagaca atcctccaa cacagcctat      240
atggaacttg ccagattgac atctgaggat tctgccatct attactgtgc aaggggggatt     300
actatggccg cttttgacta ctggggccaa ggcaccactc tcacagtctc ctca           354
```

<210> SEQ ID NO 69
<211> LENGTH: 118
<212> TYPE: PRT
<213> ORGANISM: Mus musculus

<400> SEQUENCE: 69

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Lys Phe Thr Asp Tyr
            20                  25                  30

Ala Met Tyr Trp Val Lys Gln Ser His Ala Lys Ser Leu Glu Trp Ile
        35                  40                  45

Gly Val Ile Ser Ile Tyr Tyr Gly Asn Thr Asn Tyr Asn Gln Lys Phe
    50                  55                  60

Lys Gly Lys Ala Thr Met Thr Val Asp Lys Ser Ser Asn Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Ile Thr Met Ala Ala Phe Asp Tyr Trp Gly Gln Gly Thr
            100                 105                 110

Thr Leu Thr Val Ser Ser
        115

<210> SEQ ID NO 70
<211> LENGTH: 357
<212> TYPE: DNA
<213> ORGANISM: Mus musculus

<400> SEQUENCE: 70

```
caggttactc tgaaagagtc tggccctggg atattgcagc cctcccagac cctcagtctg      60
acttgttctt tctctgggtt ttcactgagc acttttggta tgggtgtagg ctggattcgt     120
cagccttcag ggaagggtct ggagtggctg gcacacattt ggtgggatga tgataagtac     180
tataacccag ccctgaagag tcggctcaca atctccaagg atacctccaa aaaccaggta     240
ttcctcaaga tcgccaatgt ggacactgca gatactgcca catactactg tgctcgaaag     300
ggcaacttcg cctggttcac ctactggggc caagggactc tggtcactgt ctctagt        357
```

<210> SEQ ID NO 71
<211> LENGTH: 119
<212> TYPE: PRT
<213> ORGANISM: Mus musculus

<400> SEQUENCE: 71

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Lys Gly Asn Phe Ala Trp Phe Thr Tyr Trp Gly Gln Gly
            100                 105                 110

Thr Leu Val Thr Val Ser Ser
        115

<210> SEQ ID NO 72
<211> LENGTH: 354
<212> TYPE: DNA
<213> ORGANISM: Mus musculus

<400> SEQUENCE: 72
caggtccagc tgcagcagtc tgggcctgag ctggtgaggc ctggggtctc agtgaagatt      60
tcctgcaagg gttccggcta caaattcact gattatgcta tgcactgggt gaagcaaagt    120
catgcaaaga gtctagagtg gattggagtt attagtattt actatggtaa tacaaactac    180
aaccagaagt ttaaggacaa ggccacaatg actgtagaca gtcctccag cacagcctat     240
atggaacttg ccagattgac atctgaggat tctgccatct attactgtgc aaggggatt     300
actacggccg cttttgacta ctggggccaa ggcaccactc tcacagtctc ctca          354

<210> SEQ ID NO 73
<211> LENGTH: 118
<212> TYPE: PRT
<213> ORGANISM: Mus musculus

<400> SEQUENCE: 73

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Lys Phe Thr Asp Tyr
            20                  25                  30

Ala Met His Trp Val Lys Gln Ser His Ala Lys Ser Leu Glu Trp Ile
        35                  40                  45

Gly Val Ile Ser Ile Tyr Tyr Gly Asn Thr Asn Tyr Asn Gln Lys Phe
    50                  55                  60

Lys Asp Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Ile Thr Thr Ala Ala Phe Asp Tyr Trp Gly Gln Gly Thr
            100                 105                 110

Thr Leu Thr Val Ser Ser
        115

<210> SEQ ID NO 74
<211> LENGTH: 375
<212> TYPE: DNA
<213> ORGANISM: Mus musculus

<400> SEQUENCE: 74

```
caggtgcagc tggtggagtc tgggggaggc ttagtgaagc ctggagggtc cctgaaactc      60
tcctgtgcag cctctggatt caccttaagt agctatggca tgcactgggt tcgtcaggct     120
ccagagaagg ggctggagtg ggttgcagtc atatggtatg atggaagtaa taaatactat     180
gcagactccg tgaagggccg attcaccatc tccagagaca tgccaagaa caccctgttc      240
ctgcaaatga ccagtctgag gtctgaggac acggccatgt attactgtgc aagagggggt     300
ggttcgggga gttatcggta ctactactac ggtctggacg tctggggcac agggaccacg     360
gtcaccgtct ctagt                                                      375
```

<210> SEQ ID NO 75
<211> LENGTH: 125
<212> TYPE: PRT
<213> ORGANISM: Mus musculus

<400> SEQUENCE: 75

```
Gln Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Ser Tyr
            20                  25                  30

Gly Met His Trp Val Arg Gln Ala Pro Glu Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Gly Ser Gly Ser Tyr Arg Tyr Tyr Tyr Gly Leu
            100                 105                 110

Asp Val Trp Gly Thr Gly Thr Thr Val Thr Val Ser Ser
        115                 120                 125
```

<210> SEQ ID NO 76
<211> LENGTH: 357
<212> TYPE: DNA
<213> ORGANISM: Homo sapiens

<400> SEQUENCE: 76

```
caggtcaccc tgaaagagtc cggccctgcc ctggtgaagc ctacccagac cctgaccctg      60
acatgcacct tcagcggctt cagcctgagc accttcggca tgggcgtggg ctggatcaga     120
cagcctcccg gcaaggccct ggaatggctg gcccacattt ggtgggacga cgacaagtac     180
tacaacccccg ccctgaagtc ccggctgacc atcagcaagg acaccagcaa gaaccaggtg     240
gtgctgacca tgaccaacat ggaccccgtg gacaccgcca ctactactg cgcccggaag     300
ggcaacttcg cctggttcac ctactggggc cagggcaccc tggtgaccgt ctctagt        357
```

<210> SEQ ID NO 77
<211> LENGTH: 119
<212> TYPE: PRT
<213> ORGANISM: Homo sapiens

<400> SEQUENCE: 77

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Gly Asn Phe Ala Trp Phe Thr Tyr Trp Gly Gln Gly
            100                 105                 110

Thr Leu Val Thr Val Ser Ser
            115

<210> SEQ ID NO 78
<211> LENGTH: 375
<212> TYPE: DNA
<213> ORGANISM: Homo sapiens

<400> SEQUENCE: 78
caggtgcagc tggtggagtc tgggggaggc gtggtccagc ctggagggtc cctgagactc      60
tcctgtgcag cgtctggatt caccttaagt agctatggca tgcactgggt ccgccaggct     120
ccaggcaagg ggctggagtg ggtggcagtc atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagggggt     300
ggttcgggga gttatcggta ctactactac ggtctggacg tctggggcca agggaccacg     360
gtcaccgtct ctagt                                                     375

<210> SEQ ID NO 79
<211> LENGTH: 125
<212> TYPE: PRT
<213> ORGANISM: Homo sapiens

<400> SEQUENCE: 79

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Gly Ser Tyr Arg Tyr Tyr Tyr Gly Leu
            100                 105                 110

Asp Val Trp Gly Gln Gly Thr Thr Val Thr Val Ser Ser
    115                 120                 125

<210> SEQ ID NO 80
<211> LENGTH: 336
<212> TYPE: DNA
<213> ORGANISM: Mus musculus

<400> SEQUENCE: 80

```
gatgttgttc tgacccaaac tccactctct ctgcctgtca atattggaga tcaagcctct      60
atctcttgca agtctactaa gagtcttctg aatagtgatg gattcactta tttggactgg     120
tacctgcaga agccaggcca gtctccacag ctcctaatat atttggtttc taatcgattt     180
tctggagttc cagacaggtt cagtggcagt gggtcaggaa cagatttcac actcaagatc     240
agcagagtgg aggctgatga tttgggagtt tattattgct ccagagtaa ctatcttcca      300
ttcacgttcg gctcggggac aaagttggaa ataaaa                               336
```

<210> SEQ ID NO 81
<211> LENGTH: 112
<212> TYPE: PRT
<213> ORGANISM: Mus musculus

<400> SEQUENCE: 81

```
Asp Val Val Leu Thr Gln Thr Pro Leu Ser Leu Pro Val Asn Ile Gly
1               5                   10                  15
Asp Gln Ala Ser Ile Ser Cys Lys Ser Thr Lys Ser Leu Leu Asn Ser
            20                  25                  30
Asp Gly Phe Thr Tyr Leu Asp Trp Tyr Leu Gln Lys Pro Gly Gln Ser
        35                  40                  45
Pro Gln Leu Leu Ile Tyr Leu Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Asp Asp Leu Gly Val Tyr Tyr Cys Gln Ser
                85                  90                  95
Asn Tyr Leu Pro Phe Thr Phe Gly Ser Gly Thr Lys Leu Glu Ile Lys
            100                 105                 110
```

<210> SEQ ID NO 82
<211> LENGTH: 318
<212> TYPE: DNA
<213> ORGANISM: Mus musculus

<400> SEQUENCE: 82

```
caaattgttc tctcccagtc tccagcaatc ctgtctgcat ctccagggga gaaggtcaca      60
atgacttgca gggccagctc aagtgttact tacatacact ggtaccagca gaagccagga     120
tcctccccca aaccctggat ttatggcaca tccaatctgg cttctggagt ccctgttcgc     180
ttcagtggca gtgggtctgg gacctctttc tctctcacaa tcaccagagt ggaggctgaa     240
gatgctgcca cttattactg ccagcagtgg agtagtaacc cacccacgtt cggtactggg     300
accaagctgg agctgaaa                                                  318
```

<210> SEQ ID NO 83
<211> LENGTH: 106
<212> TYPE: PRT
<213> ORGANISM: Mus musculus

<400> SEQUENCE: 83

```
Gln Ile Val Leu Ser Gln Ser Pro Ala Ile Leu Ser Ala Ser Pro Gly
```

```
  1               5                  10                 15
Glu Lys Val Thr Met Thr Cys Arg Ala Ser Ser Ser Val Thr Tyr Ile
            20                  25                 30

His Trp Tyr Gln Gln Lys Pro Gly Ser Ser Pro Lys Pro Trp Ile Tyr
            35                  40                 45

Gly Thr Ser Asn Leu Ala Ser Gly Val Pro Val Arg Phe Ser Gly Ser
            50                  55                 60

Gly Ser Gly Thr Ser Phe Ser Leu Thr Ile Thr Arg Val Glu Ala Glu
65                      70                  75                 80

Asp Ala Ala Thr Tyr Tyr Cys Gln Gln Trp Ser Ser Asn Pro Pro Thr
                    85                  90                 95

Phe Gly Thr Gly Thr Lys Leu Glu Leu Lys
            100                 105

<210> SEQ ID NO 84
<211> LENGTH: 318
<212> TYPE: DNA
<213> ORGANISM: Mus musculus

<400> SEQUENCE: 84
caaattgttc tctcccagtc tccagcaatc ctgtctgcat ctccagggga gaaggtcaca      60
atgacttgca gggccagctc aagtgtaagt tacatgtact ggtaccagca gaagccagga    120
tcctccccca aaccctggat ttatgccaca tccaacctgg cttctggagt ccctgctcgc    180
ttcagtggca gtgggtctgg gacctcttac tctctcacaa tcagcagagt ggaggctgaa    240
gatgctgcca cttattactg ccagcagtgg actagtaacc cacccacgtt cggtgctggg    300
tccaagctgg agctgaga                                                  318

<210> SEQ ID NO 85
<211> LENGTH: 106
<212> TYPE: PRT
<213> ORGANISM: Mus musculus

<400> SEQUENCE: 85

Gln Ile Val Leu Ser Gln Ser Pro Ala Ile Leu Ser Ala Ser Pro Gly
1               5                  10                 15

Glu Lys Val Thr Met Thr Cys Arg Ala Ser Ser Ser Val Ser Tyr Met
            20                  25                 30

Tyr Trp Tyr Gln Gln Lys Pro Gly Ser Ser Pro Lys Pro Trp Ile Tyr
            35                  40                 45

Ala Thr Ser Asn Leu Ala Ser Gly Val Pro Ala Arg Phe Ser Gly Ser
            50                  55                 60

Gly Ser Gly Thr Ser Tyr Ser Leu Thr Ile Ser Arg Val Glu Ala Glu
65                      70                  75                 80

Asp Ala Ala Thr Tyr Tyr Cys Gln Gln Trp Thr Ser Asn Pro Pro Thr
                    85                  90                 95

Phe Gly Ala Gly Ser Lys Leu Glu Leu Arg
            100                 105

<210> SEQ ID NO 86
<211> LENGTH: 324
<212> TYPE: DNA
<213> ORGANISM: Mus musculus

<400> SEQUENCE: 86
gatatccaga tgacacagac tacatcctcc ctgtctgcct ctctgggaga cagagtcacc     60
```

```
atcagttgca gtgcaagtca gggcattagc aattatttaa actggtatca gcagaaaccg      120
gatggaactg ttaaactcct gatctattac acatcaagtt tacactcagg agtcccatca      180
aggttcagtg gcagtgggtc tgggacagat tattctctca ccatcagcaa cctggaacct      240
gaagatgttg ccacttacta ttgtcagcag tatagtaagc ttccgtacac gttcggaggg      300
gggaccaagc tggaaataag acgg                                             324
```

<210> SEQ ID NO 87
<211> LENGTH: 108
<212> TYPE: PRT
<213> ORGANISM: Mus musculus

<400> SEQUENCE: 87

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Val Ala Thr Tyr Tyr Cys Gln Gln Tyr Ser Lys Leu Pro Tyr
                85                  90                  95

Thr Phe Gly Gly Gly Thr Lys Leu Glu Ile Arg Arg
            100                 105

<210> SEQ ID NO 88
<211> LENGTH: 339
<212> TYPE: DNA
<213> ORGANISM: Mus musculus

<400> SEQUENCE: 88

```
gacattgtga tgacacagtc tccatcctcc ctgagtgtgt cagcaggaga gaaggtcact      60
atgagctgca agtccagtca gagtctgtta aacagtggaa atcaaaagaa ctacttggcc     120
tggtaccagc agaaaccagg gcagcctcct aaactgttga tctacggggc atccactagg     180
gaatctgggg tccctgatcg cttcacaggc agtggatctg gaactgattt cactcttacc     240
atcagcagtg tgcaggctga agacctggca gtttattact gtcagaatga tcatagttat     300
ccattcacgt tcggctcggg gacaaagttg gaaataaaa                            339
```

<210> SEQ ID NO 89
<211> LENGTH: 113
<212> TYPE: PRT
<213> ORGANISM: Mus musculus

<400> SEQUENCE: 89

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
                100                 105                 110

Lys

<210> SEQ ID NO 90
<211> LENGTH: 318
<212> TYPE: DNA
<213> ORGANISM: Mus musculus

<400> SEQUENCE: 90
caaattgttc tctcccagtc tccagcaatc ctgtctgcat ctccagggga gaaggtcaca    60
atgacttgca gggccagctc aagtgttact tacatacact ggtaccagca gaagccagga   120
tcctccccca aaccctggat ttatggcaca tccaatctgg cttctggagt ccctgttcgc   180
ttcagtggca gtgggtctgg gacctctttc tctctcacaa tcaccagagt ggaggctgaa   240
gatgctgcca cttattactg ccagcagtgg agtagtaacc cacccacgtt cggtactggg   300
accaagctgg agctgaaa                                                 318

<210> SEQ ID NO 91
<211> LENGTH: 106
<212> TYPE: PRT
<213> ORGANISM: Mus musculus

<400> SEQUENCE: 91

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
                20                  25                  30

His Trp Tyr Gln Gln Lys Pro Gly Ser Ser Pro Lys Pro Trp Ile Tyr
            35                  40                  45

Gly Thr Ser Asn Leu Ala Ser Gly Val Pro Val Arg Phe Ser Gly Ser
        50                  55                  60

Gly Ser Gly Thr Ser Phe Ser Leu Thr Ile Thr Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Thr Gly Thr Lys Leu Glu Leu Lys
                100                 105

<210> SEQ ID NO 92
<211> LENGTH: 339
<212> TYPE: DNA
<213> ORGANISM: Mus musculus

<400> SEQUENCE: 92
gatattgtga tgactcaggc tgcaccctct gtacctgtca cttctggaga gtcagtatcc    60
atctcctgca ggtctagtaa gagtctcctg gatcgtaatg caacacttat tttatattgg   120
ttcctgcaga ggccaggcca gtctcctcag ctcctgatat atcggatgtc caaccttgcc   180
tcaggagtcc cagacaggtt cagtggaagt gggtcgggaa gtgctttcac actgagaatc   240
agtagagtgg aggctgagga tgtgggtgtt tattactgta tgcaacatct agaatatccg   300
tacacgttcg gagggggggac caagctggaa ataaaacgg                         339

<210> SEQ ID NO 93
<211> LENGTH: 113
<212> TYPE: PRT
<213> ORGANISM: Mus musculus

<400> SEQUENCE: 93

Asp Ile Val Met Thr Gln Ala Ala Pro Ser Val Pro Val Thr Ser Gly
1               5                   10                  15

Glu Ser Val Ser Ile Ser Cys Arg Ser Lys Ser Leu Leu Asp Arg
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Ser Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg

<210> SEQ ID NO 94
<211> LENGTH: 339
<212> TYPE: DNA
<213> ORGANISM: Mus musculus

<400> SEQUENCE: 94
gatattgtga tgactcaggc tgcaccctct gtacctgtca ctcctggagc gtcagtatcc      60
atctcctgca ggtctagtaa gagtctcctg catagtaatg caacactta tttgtattgg      120 ttcctgcaga ggccaggcca gtctcctcac ctcctgatat atcggatgtc caaccttgcc     180
tcgggagtcc cagacaggtt cagtggcagt gggtcaggaa ctgctttcac actgagaatc     240
agtagagtgg aggctgagga tgtgggtgtt tattactgta tgcaacatct agaatatccg     300
tacacgttcg gagggggac caagctggaa ataaaacgg                             339

<210> SEQ ID NO 95
<211> LENGTH: 113
<212> TYPE: PRT
<213> ORGANISM: Mus musculus

<400> SEQUENCE: 95

Asp Ile Val Met Thr Gln Ala Ala Pro Ser Val Pro Val Thr Pro Gly
1               5                   10                  15

Ala Ser Val Ser Ile Ser Cys Arg Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro His Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys

Arg

<210> SEQ ID NO 96
<211> LENGTH: 339
<212> TYPE: DNA
<213> ORGANISM: Mus musculus

<400> SEQUENCE: 96

| gacattgtga tgacacagtc tccatcctcc ctggctatgt cagtaggaca gaaggtcact | 60 |
| atgagctgca gtccagtca gagccttta aatagtagca atcaaaagaa ctatttggcc | 120 |
| tggtaccagc agaaaccagg acagtctcct aaacttctga tatactttgc atccactagg | 180 |
| gaatctgggg tccctgatcg cttcataggc agtggatctg ggacagattt cactcttacc | 240 |
| atcagcagtg tgcaggctga agacctggca gattacttct gtcagcaaca ttattacact | 300 |
| ccttacacgt tcggaggggg gaccaagctg gaaataaaa | 339 |

<210> SEQ ID NO 97
<211> LENGTH: 113
<212> TYPE: PRT
<213> ORGANISM: Mus musculus

<400> SEQUENCE: 97

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Tyr Thr Pro Tyr Thr Phe Gly Gly Gly Thr Lys Leu Glu Ile
            100                 105                 110

Lys

<210> SEQ ID NO 98
<211> LENGTH: 339
<212> TYPE: DNA
<213> ORGANISM: Mus musculus

<400> SEQUENCE: 98

| gatattgtga tgactcaggc tgcaccctct gtacctgtca ctcctggaga gtcagtatcc | 60 |
| atctcctgca ggtctagtaa gagtctcctg catagtaatg caacactta cttgtattgg | 120 |
| ttcctgcaga ggccaggcca gtctcctcag ctcctgattt atcggatgtc caaccttgcc | 180 |
| tcaggagtcc cagacaggtt cagtggcagt gggtcaggaa ctgctttcac actgagaatc | 240 |
| agtagagtgg aggctgagga tgtgggtatt tattactgta tgcaacatct agaatatccg | 300 |
| tacacgttcg gagggggac caagctggaa ataaaacgg | 339 |

<210> SEQ ID NO 99
<211> LENGTH: 113
<212> TYPE: PRT

<213> ORGANISM: Mus musculus

<400> SEQUENCE: 99

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg

<210> SEQ ID NO 100
<211> LENGTH: 324
<212> TYPE: DNA
<213> ORGANISM: Mus musculus

<400> SEQUENCE: 100
gccatcaaga tgacccagtc tccatcttcc atgtatgcat ctctaggaga gagagtcact      60
atcacttgcc gggcgagtca aaatattaac aacttattag cctggttcca gcagaaacca     120
gggaaatctc ctaagaccct gatctatact gcatccagtt tgcaaagtgg ggtcccatca     180
aggttcagtg gcagtggatc tgggcaagat tattctctca ccatcagcag cctggagtat     240
gaagatatgg gaatttatta ttgtcaacag gctcatagat cccctccgac gttcggtgga     300
ggcaccaagc tggaaatcag acgt                                            324

<210> SEQ ID NO 101
<211> LENGTH: 108
<212> TYPE: PRT
<213> ORGANISM: Mus musculus

<400> SEQUENCE: 101

Ala Ile Lys Met Thr Gln Ser Pro Ser Ser Met Tyr Ala Ser Leu Gly
1               5                   10                  15

Glu Arg Val Thr Ile Thr Cys Arg Ala Ser Gln Asn Ile Asn Asn Leu
            20                  25                  30

Leu Ala Trp Phe Gln Gln Lys Pro Gly Lys Ser Pro Lys Thr Leu Ile
        35                  40                  45

Tyr Thr Ala Ser Ser Leu Gln Ser Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Gln Gln Ala His Arg Phe Pro Pro
                85                  90                  95

Thr Phe Gly Gly Gly Thr Lys Leu Glu Ile Arg Arg
            100                 105

<210> SEQ ID NO 102
<211> LENGTH: 339

```
<212> TYPE: DNA
<213> ORGANISM: Homo sapiens

<400> SEQUENCE: 102
gacatcgtga tgacccagag ccccgatagc ctggccgtgt ctctgggcga gcgggccacc      60
atcaactgca agagcagcca gagcctgctg aacagcagca accagaagaa ctacctggcc     120
tggtatcagc agaagcccgg ccagcccccc aagctgctga tctacttcgc cagcaccaga     180
gaaagcggcg tgcccgacag attttctggc agcggcagcg gcaccgactt taccctgaca     240
atcagctctc tgcaggccga ggacgtggcc gtgtacttct gccagcagca ctactacacc     300
ccctacacct tcggcggagg caccaaggtg gagatcaag                            339

<210> SEQ ID NO 103
<211> LENGTH: 113
<212> TYPE: PRT
<213> ORGANISM: Homo sapiens

<400> SEQUENCE: 103

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Tyr Thr Pro Tyr Thr Phe Gly Gly Gly Thr Lys Val Glu Ile
            100                 105                 110

Lys

<210> SEQ ID NO 104
<211> LENGTH: 324
<212> TYPE: DNA
<213> ORGANISM: Homo sapiens

<400> SEQUENCE: 104
gccatccaga tgacccagtc tccatcttcc gtgtctgctt ctataggaga cagagtcacc      60
atcacttgtc gggcgagtca aaatattaac aacttattag cctggtatca gcagaaacca     120
gggaaagccc ccaaactcct gatctatact gcatccagtt tgcaaagtga ggtcccatca     180
aggttcagcg gcagtgggtc tgggacagat ttcactctca ccatcagcag cctgcagcct     240
gaagattttg caatttactg ttgccaacag gctcatagat ccctccgac gttcggccaa      300 gggaccaagg tggaaatcag acgt                                            324

<210> SEQ ID NO 105
<211> LENGTH: 108
<212> TYPE: PRT
<213> ORGANISM: Homo sapiens

<400> SEQUENCE: 105

Ala Ile Gln Met Thr Gln Ser Pro Ser Ser Val Ser Ala Ser Ile Gly
1               5                   10                  15
```

Asp Arg Val Thr Ile Thr Cys Arg Ala Ser Gln Asn Ile Asn Asn Leu
                20                  25                  30

Leu Ala Trp Tyr Gln Gln Lys Pro Gly Lys Ala Pro Lys Leu Leu Ile
         35                  40                  45

Tyr Thr Ala Ser Ser Leu Gln Ser Glu Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Ile Tyr Cys Cys Gln Gln Ala His Arg Phe Pro Pro
                 85                  90                  95

Thr Phe Gly Gln Gly Thr Lys Val Glu Ile Arg Arg
            100                 105

<210> SEQ ID NO 106
<211> LENGTH: 106
<212> TYPE: PRT
<213> ORGANISM: Mus musculus

<400> SEQUENCE: 106

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
                20                  25                  30

Pro Lys Asp Ile Asn Val Lys Trp Lys Ile Asp Gly Ser Glu Arg Gln
         35                  40                  45

Asn Gly Val Leu Asn Ser Trp Thr Asp Gln Asp Ser Lys Asp Ser Thr
     50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                 85                  90                  95

Ile Val Lys Ser Phe Asn Arg Asn Glu Cys
            100                 105

<210> SEQ ID NO 107
<211> LENGTH: 105
<212> TYPE: PRT
<213> ORGANISM: Mus musculus

<400> SEQUENCE: 107

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
                20                  25                  30

Phe Ser Pro Ser Gly Val Thr Val Ala Trp Lys Ala Asn Gly Thr Pro
         35                  40                  45

Ile Thr Gln Gly Val Asp Thr Ser Asn Pro Thr Lys Glu Gly Asn Lys
     50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                 85                  90                  95

Lys Ser Leu Ser Pro Ala Glu Cys Leu
            100                 105

<210> SEQ ID NO 108
<211> LENGTH: 325

<212> TYPE: PRT
<213> ORGANISM: Mus musculus

<400> SEQUENCE: 108

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys Gly
                325

<210> SEQ ID NO 109
<211> LENGTH: 326
<212> TYPE: PRT
<213> ORGANISM: Homo sapiens

<400> SEQUENCE: 109

Ala Ser Thr Lys Gly Pro Ser Val Phe Pro Leu Ala Pro Cys Ser Arg
1               5                   10                  15

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 110
<211> LENGTH: 16
<212> TYPE: PRT
<213> ORGANISM: Artificial sequence
<220> FEATURE:
<223> OTHER INFORMATION: Linker

<400> SEQUENCE: 110

```
Gly Gly Gly Ser Gly Gly Gly Ser Gly Gly Gly Ser Gly Gly Gly Ser
1               5                   10                  15
```

<210> SEQ ID NO 111
<211> LENGTH: 23
<212> TYPE: PRT
<213> ORGANISM: Artificial sequence
<220> FEATURE:

<223> OTHER INFORMATION: Linker

<400> SEQUENCE: 111

Gly Ser Gly Ser Ala Thr Gly Gly Ser Gly Ser Gly Ala Ser Ser Gly
1               5                   10                  15
Ser Gly Ser Ala Thr Gly Ser
            20

<210> SEQ ID NO 112
<211> LENGTH: 12
<212> TYPE: PRT
<213> ORGANISM: Artificial sequence
<220> FEATURE:
<223> OTHER INFORMATION: Linker

<400> SEQUENCE: 112

Lys Asp Ile Asp Arg Lys Cys Cys Val Glu Cys Pro
1               5                   10

<210> SEQ ID NO 113
<211> LENGTH: 3123
<212> TYPE: DNA
<213> ORGANISM: Homo sapiens

<400> SEQUENCE: 113

| | | | | | |
|---|---|---|---|---|---|
| atcagtctcc | gcacgcggtt | ccgcaggtgg | cagcgatggc | ccagtcctga | actcccgcc | 60 |
| atggccggcg | ccccggccc | gctgcgcctt | gcgctgctgc | tgctcgggat | ggtgggcagg | 120 |
| gccggccccc | gcccccaggg | tgccactgtg | tccctctggg | agacggtgca | gaaatgcgga | 180 |
| gaataccgac | gccagtgcca | gcgctccctg | actgaggatc | cacctcctgc | cacagacttg | 240 |
| ttctgcaacc | ggaccttcga | tgaatacgcc | tgctggccag | atgggagcc | aggctcgttc | 300 |
| gtgaatgtca | gctgccccctg | gtacctgccc | tgggccagca | gtgtgccgca | gggccacgtg | 360 |
| taccggttct | gcacagctga | aggcctctgg | ctgcagaagg | acaactccag | cctgccctgg | 420 |
| agggacttgt | cggagtgcga | ggagtccaag | cgaggggaaa | gaagctcccc | ggaggagcag | 480 |
| ctcctgttcc | tctacatcat | ctacacggtg | ggctacgcac | tctccttctc | tgctctggtt | 540 |
| atcgcctctg | cgatcctcct | cggcttcaga | cacctgcact | gcaccaggaa | ctacatccac | 600 |
| ctgaacctgt | ttgcatcctt | catcctgcga | gcattgtccg | tcttcatcaa | ggacgcagcc | 660 |
| ctgaagtgga | tgtatagcac | agccgcccag | cagcaccagt | gggatgggct | cctctcctac | 720 |
| caggactctc | tgagctgccg | cctggtgttt | ctgctcatgc | agtactgtgt | ggcggccaat | 780 |
| tactactggc | tcttggtgga | gggcgtgtac | ctgtacacac | tgctggcctt | ctcggtctta | 840 |
| tctgagcaat | ggatcttcag | gctctacgtg | agcataggct | ggggtgttcc | cctgctgttt | 900 |
| gttgtccccct | gggcattgt | caagtacctc | tatgaggacg | agggctgctg | gaccaggaac | 960 |
| tccaacatga | actactggct | cattatccgg | ctgcccattc | tctttgccat | ggggtgaac | 1020 |
| ttcctcatct | ttgttcgggt | catctgcatc | gtggtatcca | aactgaaggc | caatctcatg | 1080 |
| tgcaagacag | acatcaaatg | cagacttgcc | aagtccacgc | tgacactcat | cccctgctg | 1140 |
| gggactcatg | aggtcatctt | tgcctttgtg | atggacgagc | acgccgggg | gaccctgcgc | 1200 |
| tcatcaagc | tgtttacaga | gctctccttc | acctccttcc | aggggctgat | ggtggccata | 1260 |
| ttatactgct | tgtcaacaa | tgaggtccag | ctggaatttc | ggaagagctg | ggagcgctgg | 1320 |
| cggcttgagc | acttgcacat | ccagagggac | agcagcatga | gcccctcaa | gtgtcccacc | 1380 |
| agcagcctga | gcagtggagc | cacggcgggc | agcagcatgt | acacagccac | ttgccaggcc | 1440 |

-continued

```
tcctgcagct gagactccag cgcctgccct cctgggggtc cttgctgcag gccgggtggc    1500
caatccaggt gggagagaca ctcccaggga caagggaagg aagggacaca cacacacaca    1560
cacacacaca cacacacaca cacatacatc ctgctttccc tccccaaacc catcagacag    1620
gtaaatgggc agtgcctcct ggaccatggg acacattttc tcctaggaga agcagcctcc    1680
taatttgatc acagtggcga gaggagagga aaaacgatcg ctgtgaaaat gaggaggatt    1740
gcttcttgtg aaaccacagg cccttggggt tcccccagac agagccgcaa atcaaccccca   1800 gactcaaact caaggtcaac ggcttattag tgaaactggg gcttgcaaga ggaggtggtt    1860
ctgaaagtgg ctcttctaac ctcagccaaa cacagagcgg gagtgacggg agcctcctct    1920
gcttgcatca cttggggtca ccaccctccc ctgtcttctc tcaaagggaa gctgtttgtg    1980
tgtctgggtt gcttatttcc ctcatcttgc cccctcatct cactgcccag tttcttttttg   2040 aggggctttg tttgggccac tgccagcagc tgtttctgga aatggctgta ggtggtgttg    2100
agaaagaatg agcattgaga cggtgctcgc ttctcctcca ggtatttgag ttgttttggt    2160
gcctgcctct gccatgccca gagaatcagg gcaggcttgc caccggggaa cccagccctg    2220
gggtatgagc tgccaagtct attttaaaga cgctcaagaa tcctctgggg ttcatctagg    2280
gacacgttag gaatgtccag actgtgggtg tagattacct gccacttcca ggagcccaga    2340
gggccaagag agacattgcc tccacctctc cttggaaata ctttatctgt gaccacacgc    2400
tgtctcttga gaatttggat acactctcta gctttagggg accatgaaga gactctctta    2460
gggaaaccaa tagtccccat cagcaccatg gaggcaggct cccctgcct ttgaaattcc      2520 cccacttggg agcttgtata tacttcactc acttttcttt attgctgtga atagtctgtg    2580
tgcacaatgg gcaattctga cttctcccat ctagtggaaa tgagcgaaat catggttgta   2640
gtgatgttgt ttgggagagt gcagtagtaa ttgatttgac ccactcacac ttggagctaa    2700
ttaaggtttg ccctgcctgc agcctccccc acaaataatg aacagcagaa agactggacg    2760
gggaaaccta tcaatcctgc ccccagccat ggtgaggaag ccccaagcca tggtgacaca    2820
cagcagcact gcagatagcc agacacatgg ctatcctaga gaggctggca aggagttcgt    2880
ggctgcaaaa gaagtttctg gagcaagaga gagctcgctc ttgggagtca ggacctccgg    2940
ggagagcaga gggttccgac ggattccttt atgagtcagt ctctctctcc cttttaaatg    3000
gtgggaaccc tccccaaaac cttttcccag acacattctc ctgtgcccct cagagaggca    3060
tgtgatgtgc aaggaaaata ataggatata aaacacatca agtagaaaat ttcttatact    3120
tca                                                                  3123
```

<210> SEQ ID NO 114
<211> LENGTH: 463
<212> TYPE: PRT
<213> ORGANISM: Homo sapiens

<400> SEQUENCE: 114

```
Met Ala Gly Ala Pro Gly Pro Leu Arg Leu Ala Val Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
```

-continued

```
                65                  70                  75                  80
        Val Asn Val Ser Cys Pro Trp Tyr Leu Pro Trp Ala Ser Ser Val Pro
                        85                  90                  95

Gln Gly His Val Tyr Arg Phe Cys Thr Ala Glu Gly Leu Trp Leu Gln
                    100                 105                 110

Lys Asp Asn Ser Ser Leu Pro Trp Arg Asp Leu Ser Glu Cys Glu Glu
                    115                 120                 125

Ser Lys Arg Gly Glu Arg Ser Ser Arg Glu Gln Leu Leu Phe Leu
            130                 135                 140

Tyr Ile Ile Tyr Thr Val Gly Tyr Ala Leu Ser Phe Ser Ala Leu Val
        145                 150                 155                 160

Ile Ala Ser Ala Ile Leu Leu Gly Phe Arg His Leu His Cys Thr Arg
                        165                 170                 175

Asn Tyr Ile His Leu Asn Leu Phe Ala Ser Phe Ile Leu Arg Ala Leu
                    180                 185                 190

Ser Val Phe Ile Lys Asp Ala Ala Leu Lys Trp Met Tyr Ser Thr Ala
                    195                 200                 205

Ala Gln Gln His Gln Trp Asp Gly Leu Leu Ser Tyr Gln Asp Ser Leu
                    210                 215                 220

Ser Cys Arg Leu Val Phe Leu Leu Met Gln Tyr Cys Val Ala Ala Asn
        225                 230                 235                 240

Tyr Tyr Trp Leu Leu Val Glu Gly Val Tyr Leu Tyr Thr Leu Leu Ala
                        245                 250                 255

Phe Ser Val Phe Ser Glu Gln Trp Ile Phe Arg Leu Tyr Val Ser Ile
                    260                 265                 270

Gly Trp Gly Val Pro Leu Leu Phe Val Val Pro Trp Gly Ile Val Lys
                    275                 280                 285

Tyr Leu Tyr Glu Asp Glu Gly Cys Trp Thr Arg Asn Ser Asn Met Asn
                    290                 295                 300

Tyr Trp Leu Ile Ile Arg Leu Pro Ile Leu Phe Ala Ile Gly Val Asn
        305                 310                 315                 320

Phe Leu Ile Phe Val Arg Val Ile Cys Ile Val Val Ser Lys Leu Lys
                        325                 330                 335

Ala Asn Leu Met Cys Lys Thr Asp Ile Lys Cys Arg Leu Ala Lys Ser
                    340                 345                 350

Thr Leu Thr Leu Ile Pro Leu Leu Gly Thr His Glu Val Ile Phe Ala
                    355                 360                 365

Phe Val Met Asp Glu His Ala Arg Gly Thr Leu Arg Phe Ile Lys Leu
                    370                 375                 380

Phe Thr Glu Leu Ser Phe Thr Ser Phe Gln Gly Leu Met Val Ala Ile
        385                 390                 395                 400

Leu Tyr Cys Phe Val Asn Asn Glu Val Gln Leu Glu Phe Arg Lys Ser
                        405                 410                 415

Trp Glu Arg Trp Arg Leu Glu His Leu His Ile Gln Arg Asp Ser Ser
                    420                 425                 430

Met Lys Pro Leu Lys Cys Pro Thr Ser Ser Leu Ser Ser Gly Ala Thr
                    435                 440                 445

Ala Gly Ser Ser Met Tyr Thr Ala Thr Cys Gln Ala Ser Cys Ser
                    450                 455                 460

<210> SEQ ID NO 115
<211> LENGTH: 20
<212> TYPE: DNA
<213> ORGANISM: Artificial sequence
```

```
<220> FEATURE:
<223> OTHER INFORMATION: Primer

<400> SEQUENCE: 115
tttggrggga agatgaagac                                                    20

<210> SEQ ID NO 116
<211> LENGTH: 21
<212> TYPE: DNA
<213> ORGANISM: Artificial sequence
<220> FEATURE:
<223> OTHER INFORMATION: Primer

<400> SEQUENCE: 116
ttaacactct cccctgttga a                                                  21

<210> SEQ ID NO 117
<211> LENGTH: 21
<212> TYPE: DNA
<213> ORGANISM: Artificial sequence
<220> FEATURE:
<223> OTHER INFORMATION: Primer

<400> SEQUENCE: 117
ttaacactca ttcctgttga a                                                  21

<210> SEQ ID NO 118
<211> LENGTH: 21
<212> TYPE: DNA
<213> ORGANISM: Artificial sequence
<220> FEATURE:
<223> OTHER INFORMATION: Primer

<400> SEQUENCE: 118
tggacaggga tccagagttc c                                                  21

<210> SEQ ID NO 119
<211> LENGTH: 21
<212> TYPE: DNA
<213> ORGANISM: Artificial sequence
<220> FEATURE:
<223> OTHER INFORMATION: Primer

<400> SEQUENCE: 119
tggacagggc tccatagttc c                                                  21

<210> SEQ ID NO 120
<211> LENGTH: 20
<212> TYPE: DNA
<213> ORGANISM: Artificial sequence
<220> FEATURE:
<223> OTHER INFORMATION: Primer

<400> SEQUENCE: 120
actcgtcctt ggtcaacgtg                                                    20

<210> SEQ ID NO 121
<211> LENGTH: 23
<212> TYPE: DNA
<213> ORGANISM: Artificial sequence
<220> FEATURE:
<223> OTHER INFORMATION: Primer

<400> SEQUENCE: 121
ccaccatgga ctttgggctg agc                                                23
```

```
<210> SEQ ID NO 122
<211> LENGTH: 20
<212> TYPE: DNA
<213> ORGANISM: Artificial sequence
<220> FEATURE:
<223> OTHER INFORMATION: Primer

<400> SEQUENCE: 122
agagccggtg gcagagccag                                                    20

<210> SEQ ID NO 123
<211> LENGTH: 43
<212> TYPE: DNA
<213> ORGANISM: Artificial sequence
<220> FEATURE:
<223> OTHER INFORMATION: Primer

<400> SEQUENCE: 123
ctggctctgc caccggctct gccatccaga tgacccagtc tcc                          43

<210> SEQ ID NO 124
<211> LENGTH: 22
<212> TYPE: DNA
<213> ORGANISM: Artificial sequence
<220> FEATURE:
<223> OTHER INFORMATION: Primer

<400> SEQUENCE: 124
acactctccc ctgttgaagc tc                                                 22

<210> SEQ ID NO 125
<211> LENGTH: 31
<212> TYPE: DNA
<213> ORGANISM: Artificial sequence
<220> FEATURE:
<223> OTHER INFORMATION: Primer

<400> SEQUENCE: 125
ccggctagcc accatggact ttgggctgag c                                       31

<210> SEQ ID NO 126
<211> LENGTH: 36
<212> TYPE: DNA
<213> ORGANISM: Artificial sequence
<220> FEATURE:
<223> OTHER INFORMATION: Primer

<400> SEQUENCE: 126
agtgcggccg ctcaacactc tccctgttg aagctc                                   36

<210> SEQ ID NO 127
<211> LENGTH: 39
<212> TYPE: PRT
<213> ORGANISM: Heloderma suspectum

<400> SEQUENCE: 127

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```